US010682398B2

(12) United States Patent
Faulkner et al.

(10) Patent No.: US 10,682,398 B2
(45) Date of Patent: Jun. 16, 2020

(54) YEAST VACCINE VECTOR INCLUDING IMMUNOSTIMULATORY AND ANTIGENIC POLYPEPTIDES AND METHODS OF USING THE SAME

(71) Applicants: THE BOARD OF TRUSTEES OF THE UNIVERSITY OF ARKANSAS, Little Rock, AR (US); The Texas A&M University System, College Station, TX (US)

(72) Inventors: Olivia B. Faulkner, Shawnee, KS (US); Lisa Bielke, Wooster, OH (US); Leona Nicole Calhoun, Fayetteville, AR (US); Luc Berghman, College Station, TX (US); Billy Hargis, Fayetteville, AR (US)

(73) Assignees: THE TEXAS A&M UNIVERSITY SYSTEM, College Station, TX (US); THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 23 days.

(21) Appl. No.: 15/585,488

(22) Filed: May 3, 2017

(65) Prior Publication Data
US 2017/0319671 A1 Nov. 9, 2017

Related U.S. Application Data

(60) Provisional application No. 62/331,044, filed on May 3, 2016.

(51) Int. Cl.
| *A61K 39/00* | (2006.01) |
| *A61K 39/39* | (2006.01) |
| *A61K 39/112* | (2006.01) |
| *A61K 39/395* | (2006.01) |
| *A61K 39/02* | (2006.01) |
| *A61K 39/08* | (2006.01) |
| *A61K 39/108* | (2006.01) |
| *A61K 39/015* | (2006.01) |
| *C07K 14/395* | (2006.01) |
| *C07K 14/47* | (2006.01) |
| *C12N 15/63* | (2006.01) |
| *C07K 14/39* | (2006.01) |
| *A61K 39/012* | (2006.01) |

(52) U.S. Cl.
CPC ............ *A61K 39/00* (2013.01); *A61K 39/015* (2013.01); *A61K 39/0258* (2013.01); *A61K 39/0275* (2013.01); *A61K 39/08* (2013.01); *A61K 39/107* (2013.01); *A61K 39/39558* (2013.01); *C07K 14/39* (2013.01); *C07K 14/395* (2013.01); *C07K 14/47* (2013.01); *C12N 15/63* (2013.01); *A61K 2039/523* (2013.01); *A61K 2039/70* (2013.01); *C07K 2319/00* (2013.01); *C07K 2319/40* (2013.01); *Y02A 50/482* (2018.01)

(58) Field of Classification Search
CPC .......... A61K 2039/523; A61K 2039/70; A61K 39/00; A61K 39/0005; A61K 39/012; A61K 39/015; A61K 39/0258; A61K 39/0275; A61K 39/08; A61K 39/107; A61K 39/225; A61K 39/39558; C07K 14/39; C07K 14/395; C07K 14/47; C07K 14/70575; C07K 2319/00; C07K 2319/40; C12N 15/63; C12N 15/1034; Y02A 50/482
See application file for complete search history.

(56) References Cited

U.S. PATENT DOCUMENTS

| 5,683,700 A | 11/1997 | Charles et al. |
| 5,747,309 A | 5/1998 | Allan et al. |
| 5,962,406 A | 10/1999 | Armitage et al. |
| 5,981,724 A | 11/1999 | Armitage et al. |
| 6,087,329 A | 7/2000 | Armitage et al. |
| 6,190,669 B1 | 2/2001 | Noriega et al. |
| 6,264,951 B1 | 7/2001 | Armitage et al. |
| 6,306,387 B1 | 10/2001 | Galan |
| 6,410,711 B1 | 6/2002 | Armitage et al. |
| 6,479,258 B1 | 11/2002 | Short |
| 6,713,279 B1 | 3/2004 | Short |
| 6,902,906 B1 | 6/2005 | Chatfield |
| 6,923,957 B2 | 8/2005 | Lowery et al. |
| 6,923,958 B2 | 8/2005 | Xiang et al. |
| 6,936,425 B1 | 8/2005 | Hensel et al. |
| 6,969,609 B1 | 11/2005 | Schlom et al. |
| 7,087,573 B1 | 8/2006 | Lazarus et al. |

(Continued)

FOREIGN PATENT DOCUMENTS

| WO | WO 1993/008207 | 4/1993 |
| WO | WO 1995/014487 | 6/1995 |

(Continued)

OTHER PUBLICATIONS

Restriction Requirement in U.S. Appl. No. 14/623,105 dated Jan. 4, 2016.
Office Action for U.S. Appl. No. 14/623,105 dated Jun. 15, 2016.
Office Action for U.S. Appl. No. 14/623,105 dated Jan. 12, 2017.
Holmgren, J. et al., "Mucosal immunity: implications for vaccine development," Immunobiol. (1992) 184:157-179.
Kaiser, J., "A one-size-fits-all flu vaccine?," Science (2006) 312:380-382.

(Continued)

Primary Examiner — Sarvamangala Devi
(74) Attorney, Agent, or Firm — Quarles & Brady LLP

(57) ABSTRACT

Vaccine compositions including a yeast comprising an immunostimulatory polypeptide and optionally an antigenic polypeptide are provided herein. The immunostimulatory polypeptide and the antigenic polypeptide are expressed or displayed on the surface of the yeast vaccine composition. Methods of using the vaccine composition to vaccinate subjects are also provided.

13 Claims, 7 Drawing Sheets

Specification includes a Sequence Listing.

(56) References Cited

U.S. PATENT DOCUMENTS

| | | |
|---|---|---|
| 7,118,751 B1 | 10/2006 | Ledbetter et al. |
| 7,288,250 B2 | 10/2007 | Newman et al. |
| 7,332,298 B2 | 2/2008 | Kornbluth |
| 7,371,392 B2 | 5/2008 | Tripp et al. |
| 7,405,270 B2 | 7/2008 | Armitage et al. |
| 7,495,090 B2 | 2/2009 | Prussak et al. |
| 7,842,501 B2 | 11/2010 | Cai et al. |
| 7,928,213 B2 | 4/2011 | Prussak et al. |
| 8,163,281 B2 | 4/2012 | Liu et al. |
| 8,541,208 B1 * | 9/2013 | Plesch .................. C07K 14/245 435/106 |
| 8,604,178 B2 | 12/2013 | Bottje et al. |
| 8,673,580 B2 | 3/2014 | Tamai et al. |
| 8,865,653 B2 | 10/2014 | Zitvogel |
| 8,906,634 B2 | 12/2014 | Gougen et al. |
| 8,956,618 B2 | 2/2015 | Berghman |
| 8,956,849 B2 | 2/2015 | Bottje et al. |
| 8,961,990 B2 | 2/2015 | Hargis et al. |
| 9,125,854 B2 | 9/2015 | Bottje et al. |
| 9,164,107 B2 | 10/2015 | Gougeon et al. |
| 9,226,957 B2 | 1/2016 | Bottje et al. |
| 9,708,661 B2 | 7/2017 | Shi et al. |
| 2001/0021386 A1 | 9/2001 | Nuijten et al. |
| 2003/0045492 A1 | 3/2003 | Tang et al. |
| 2003/0165538 A1 | 9/2003 | Goldman et al. |
| 2004/0006006 A9 | 1/2004 | Armitage et al. |
| 2004/0047873 A1 | 3/2004 | Al-Shamkhani et al. |
| 2004/0053841 A1 | 3/2004 | Tracey et al. |
| 2004/0141948 A1 | 7/2004 | O'Keefe |
| 2004/0156851 A1 | 8/2004 | Newman |
| 2004/0203039 A1 | 10/2004 | Hensel et al. |
| 2004/0242481 A1 | 12/2004 | Bianchi et al. |
| 2005/0181994 A1 | 8/2005 | Chamberlain et al. |
| 2005/0226888 A1 | 10/2005 | Deisseroth et al. |
| 2006/0014248 A1 | 1/2006 | Marshall et al. |
| 2006/0078994 A1 | 4/2006 | Healey et al. |
| 2006/0121047 A1 | 6/2006 | Tracey |
| 2006/0233829 A1 | 10/2006 | Curtiss |
| 2006/0286074 A1 | 12/2006 | Tang et al. |
| 2007/0025982 A1 | 2/2007 | Ledbetter et al. |
| 2007/0082400 A1 | 4/2007 | Healey et al. |
| 2007/0128183 A1 | 6/2007 | Meinke et al. |
| 2007/0128223 A1 | 6/2007 | Tang et al. |
| 2007/0237779 A1 | 10/2007 | Ledbetter et al. |
| 2007/0249553 A1 | 10/2007 | Newell et al. |
| 2008/0004207 A1 | 1/2008 | Tsung et al. |
| 2008/0069821 A1 | 3/2008 | Yang et al. |
| 2008/0075728 A1 | 3/2008 | Newman |
| 2008/0102079 A1 | 5/2008 | Ainley et al. |
| 2008/0124320 A1 | 5/2008 | O'Keefe |
| 2008/0305120 A1 | 12/2008 | Messmer et al. |
| 2009/0004194 A1 | 1/2009 | Kedl |
| 2010/0040608 A1 | 2/2010 | Wahren-Herlenius et al. |
| 2010/0047231 A1 | 2/2010 | Zabaleta Azpiroz et al. |
| 2010/0074915 A1 | 3/2010 | Hayes |
| 2010/0112002 A1 | 5/2010 | Lien et al. |
| 2010/0196419 A1 | 8/2010 | Compans et al. |
| 2010/0233152 A1 | 9/2010 | Bullerdiek |
| 2010/0291109 A1 | 11/2010 | Kedl |
| 2010/0292309 A1 | 11/2010 | Vile et al. |
| 2011/0020318 A1 | 1/2011 | Tracey et al. |
| 2011/0111015 A1 | 5/2011 | Bottje |
| 2011/0159026 A1 | 6/2011 | Bottje |
| 2012/0282291 A1 | 11/2012 | Berghman et al. |
| 2013/0084304 A1 | 4/2013 | Hargis et al. |
| 2014/0093534 A1 | 4/2014 | Bottje |
| 2015/0150958 A1 | 6/2015 | Pillich |
| 2015/0190500 A1 | 7/2015 | Berghman et al. |
| 2016/0000895 A1 | 1/2016 | Barta |
| 2016/0038581 A1 | 2/2016 | Bielke et al. |

FOREIGN PATENT DOCUMENTS

| | | |
|---|---|---|
| WO | WO 1996/026735 | 9/1996 |
| WO | WO 1996/040918 | 12/1996 |
| WO | WO 1999/027948 | 6/1999 |
| WO | WO 1999/032138 | 7/1999 |
| WO | WO 1999/059609 | 11/1999 |
| WO | WO 2000/063395 | 10/2000 |
| WO | WO 2000/063405 | 10/2000 |
| WO | WO 2001/042298 | 6/2001 |
| WO | WO 2001/056602 | 8/2001 |
| WO | WO 2002/036769 | 5/2002 |
| WO | WO 2002/092773 | 11/2002 |
| WO | WO 2003/026691 | 4/2003 |
| WO | WO 2003/099340 | 12/2003 |
| WO | WO 2004/009615 | 1/2004 |
| WO | WO 2004/046338 | 6/2004 |
| WO | WO 2004/046345 | 6/2004 |
| WO | WO 2005/025604 | 3/2005 |
| WO | WO 2005/035570 | 4/2005 |
| WO | WO 2005/049641 | 6/2005 |
| WO | WO 2005/058950 | 6/2005 |
| WO | WO 2005/113598 | 12/2005 |
| WO | WO 2006/012373 | 2/2006 |
| WO | WO 2006/042177 | 4/2006 |
| WO | WO 2006/105972 | 10/2006 |
| WO | WO 2007/011606 | 1/2007 |
| WO | WO 2007/042583 | 4/2007 |
| WO | WO 2007/054658 | 5/2007 |
| WO | WO 2007/056266 | 5/2007 |
| WO | WO 2007/103048 | 9/2007 |
| WO | WO 2007/117682 | 10/2007 |
| WO | WO 2008/036675 | 3/2008 |
| WO | WO 2008/109825 | 9/2008 |
| WO | WO 2009/059018 | 5/2009 |
| WO | WO 2009/059298 | 5/2009 |
| WO | 2011/036564 A2 | 3/2011 |
| WO | WO 2011/156619 A2 * | 12/2011 |
| WO | WO 2014/028776 | 2/2014 |
| WO | WO 2014/152508 * | 9/2014 |

OTHER PUBLICATIONS

Katz, J.M. et al., "Adjuvant activity of the heat-labile enterotoxin from enterotoxigenic *Escherichia coli* for oral administration of inactivated influenza virus vaccine," J. Infect. Dis. (1997) 175:352-363.

Kim, E.-H. et al., "Prokaryote-expressed M2e protein improves H9N2 influenza vaccine efficacy and protection against lethal influenza in virus in mice," Virol. J.. (2013) 10(104):1-11.

Kimura, R. et al., "Enhancement of antibody response by high mobility group box protein-1-based DNA immunization," J. of Immunol. Methods (2010) 361:21-30.

Koch, F. et al., "High level IL-12 production by murine dendritic cells: upregulation via MHC class II and CD40 molecules and downregulation by IL-4 and IL-10," J. Exp. Med. (1996) 184:741-746.

Kodihalli, S. et al., "Cross-protection among lethal H5N2 influenza viruses induced by DNA vaccine to the hemagglutinin," J. Virol. (1997) 71:3391-3396.

Lavelle, E.C. et al., "Delivery systems and adjuvants for oral vaccines," Expert Opin. Drug Deliv. (2006) 3(6):747-762.

Layton, S.L., et al., "Vaccination of chickens with recombinant *Salmonella* expressing M2e and CD154 epitopes increases protection and decreases viral shedding after low pathogenic avian influenza challenge," Poultry Science (2009) 88(11):2244-2252.

Layton et al., Evaluation of *Salmonella*-vectored Campylobacter peptide epitopes for reduction of Campylobacter jejuni in broiler chickens, Clin. Vaccine Immunol. (2011) 18(3):449-454.

Lee, J. et al., "Mucosal immunization with surface-displayed severe acute respiratory syndrome coronavirus spike protein on Lactobacillus casei induces neutralizing antibodies in mice," J. Virol. (2006) 80:4079-4087.

Lee, J.S. et al., "Surface-displayed viral antigens on *Salmonella* carrier vaccine," Nat. Biotechnol. (2000) 18:645-648.

(56) References Cited

OTHER PUBLICATIONS

Li, W., "Synergistic antibody induction by antigen-CD40 ligand fusion protein as improved immunogen," Immunology (2005) 115(2):215-222.

Liu, W. et al., "Monoclonal antibodies recognizing EVETPIRN epitope of influenza A virus M2 protein could protect mice from lethal influenza A virus challenge," Immunol. Lett. (2004) 93:131-136.

Liu, W. et al., "Sequence comparison between the extracellular domain of M2 protein human and avian influenza A virus provides new information for bivalent influenza vaccine design," Microbes and Infection (2005) 7:171-177.

Liu, M. et al., "Display of avian influenza virus nucleoprotein on Bacillus thuringiensis cell surface using CTC as a fusion partner," Applied Genetics and Molecular Biotechnology (2008) 78:669-676.
Mann, J.F. et al., "Delivery systems: a vaccine strategy for overcoming mucosal tolerance?" Expert Rev. Vaccines (2009) 8(1):103-112.
Manoj, S. et al., "Targeting with Bovine CD154 enhances humoral immune responses induced by a DNA vaccine in sheep," (2003) Journal of Immunology 170:989-996.
Mendoza, R.B. et al., "Cutting edge: Immunostimulatory effects of a plasmid expressing CD40 ligand (CD154) on gene immunization," Journal of Immunology (1997) 159(12):5777-5781.
Miga, A. et al., "The role of CD40-CD154 interactions in the regulation of cell mediated immunity," Immunol. Invest. (2000) 29:111-114.
Mogensen, T.H., "Pathogen recognition and inflammatory signaling in innate immune defenses," Clin. Microbiol. Rev. (2009) 22(2):240-273.
Mohamadzadeh, M. et al., "Targeting mucosal dendritic cells with microbial antigens from probiotic lactic acid bacteria," Expert Rev. Vaccines (2008) 7(2):163-174.
Moyle, P.M. et al., "Mucosal immunisation: adjuvants and delivery systems," Curr. Drug Deliv. (2004) 1(4):385-396.
Mozdzanowska, K. et al., "Induction of influenza type A virus-specific resistance by immunization of mice with a synthetic multiple antigenic peptide vaccine that contains ectodomains of matrix protein 2," Vaccine (2003) 21:2616-2626.
Muthumani, G. et al., "Co-immunization with an optimized plasmid-encoded immune stimulatory interleukin, high-mobility group box 1 protein, results in enhanced interferon-y secretion by antigen-specific CD8 T cells," Immunology (2009) 128: e612-e620.
Nakajima, A. et al., "Antitumor effect of CD40 ligand: Elicitation of local and systemic antitumor responses by IL-12 and B7," (1998) Journal of Immunology 161:1901-1907.
Neirynck, S. et al., "A universal influenza A vaccine based on the extracellular domain of the M2 protein," Nat. Med. (1999) 5:1157-1163.
Ninomiya, A. et al., "Intranasal administration of a synthetic peptide vaccine encapsulated in liposome together with an anti-CD40 antibody induces protective immunity against influenza A virus in mice," Vaccine (2002) 20:3123-3129.
Palese, P. et al., "Influenza vaccines: present and future," J. Clin. Invest. (2002) 110:9-13.
Pisetsky, D.S. et al., "High-mobility group box protein 1 (HMGB1): an alarmin mediating the pathogenesis of rheumatic disease," Arthritis Res. Ther. (2008) 10(3):209.
Rovere-Querini, P. et al., "HMGB1 is an endogenous immune adjuvant released by necrotic cells," EMBO Rep. (2004) 5(8):825-830.
Saenz, R. et al., "HMGB1-derived peptide acts as adjuvant inducing immune responses to peptide and protein antigen," (2010) Vaccine 28(47):7556-7562.
Slepushkin, V.A. et al., "Protection of mice against influenza A virus challenge by vaccination with baculovirus-expressed M2 protein," Vaccine (1995) 13:1399-1402.
Stubbs, A.C. et al., "Whole recombinant yeast vaccine activates dendritic cells and elicits protective cell-mediated immunity," Nat. Med. (2001) 7:625-629.
Swayne, D.E., "Vaccines for List A poultry diseases: emphasis on avian influenza," Dev. Biol. (2003) 114:201-212.
Tompkins, S.M. et al., "Matrix protein 2 vaccination and protection against influenza viruses, including subtype H5N1," Emerging Infectious Diseases (2007) 13(3):426-435.
Tresgaskes, C.A. et al., "Conservation of biological properties of the CD40 ligand, CD154 in a non-mammalian vertebrate," Dev. Comp. Immunol. (2005) 29:361-374.
Ulloa, L. et al., "High-mobility group box 1 (HMGB1) protein: friend and foe," Cytokine Growth Factor Rev. (2006) 17(3):189-201.
Vega, M.L. et al., "A *Salmonella typhi* OmpC fusion protein expressing the CD154 Trp140-Ser149 amino acid strand binds CD40 and activates a lymphoma B-cell line," Immunol. (2003) 110:206-216.
Xu, Y. et al., "The role of CD40-CD154 interaction in cell immunoregulation," J. Biomed. Sci. (2004) 11:426-438.
Zharikova, D. et al., "Influenza type A virus escape mutants emerge in vivo in the presence of antibodies to the ectodomain of matrix protein 2," J. Virol. (2005) 79:6644-6654.
Zou, P. et al., "The epitope recognized by a monoclonal antibody in influenza A virus M2 protein is immunogenic and confers immune protection," Int. Immunopharmacol. (2005) 5:631-635.
International Search Report and Written Opinion of the International Searching Authority for Application No. PCT/US07/78785 dated Sep. 29, 2008 (11 pages).
International Search Report and Written Opinion of the International Searching Authority for Application No. PCT/US11/22062 dated Mar. 29, 2011 (11 pages).
International Search Report and Written Opinion of the International Searching Authority for Application No. PCT/US11/39832 dated Nov. 23, 2011 (15 pages).
Restriction Requirement in U.S. Appl. No. 13/574,504 dated Jul. 9, 2013.
Office Action for U.S. Appl. No. 13/574,504 dated Dec. 12, 2013.
Office Action for U.S. Appl. No. 13/574,504 dated Jun. 18, 2014.
Agterberg, M. et al., "Outer membrane protein PhoE as a carrier for the exposure of foreign antigenic determinants at the bacterial cell surface," Antonie Van Leeuwenhoek (1991) 59(4):249-262.
Al-Ramadi, B. K. et al., "Induction of innate immunity by IL-2 expressing *Salmonella* confers protection against letal challenge," Mol. Immunol. (2003) 39:763-770.
Al-Ramadi, B. K. et al., "Influence of vector-encoded cytokines on anti-*Salmonella* immunity: divergent effects of interleukin-2 and tumor necrosis factor alpha," Infect. Immun. (2001) 69:3960-3988.
Andersson, U. et al., "HMGB1 is a therapeutic target for sterile inflammation and infection," Annu. Rev. Immunol. (2011) 29:139-162.
Anonymous. Who. Fact sheet No. 139. (http://www.who.int/mediacentre/factsheets/fs139/en/). 2005.
Babu, U., et al., "*Salmonella* enteritidis clearance and immune responses in chickens following *Salmonella* vaccination and challenge," Vet. Immunol. Immunopathol. (2004)101:251-257.
Barr, T.A. et al., "A potent adjuvant effect of CD40 antibody attached to antigen," Immunology (2003) 109:87-92.
Barrow, P. A., et al., "Reduction in faecal excretion of *Salmonella typhimurium* strain F98 in chickens vaccinated with live and killed *S. typhimurium* organisms," Epidemiol. Infect. (1990) 104:413-426.
Black, R.A. et al., "Antibody response to the M2 protein of influenza A virus expressed in insect cells," J. Gen. Virol. (1993) 74(Pt.1):143-146.
Blomfield, I.C. et al., "Allelic exchange in *Escherichia coli* using the Bacillus subtilis sacB gene and a temperature-sensitive pSC101 replicon," Mol Microbial (1991) 5(6):1447-1457.
Buckley, A.M. et al., "Evaluation of live-attenuated *Salmonella* vaccines expressing Campylobacter antigens for control of C. jejuni in poultry," (2010) Vaccine 28(4):1094-1105.
Capua, I. et al., "The challenge of avian influenza to the veterinary community," Avian Pathol. (2006) 35:189-205.
Capua, I. et al., "Vaccination for avian influenza in Asia," Vaccine (2004) 22:4137-4138.
Capua, I. et al, "Control of avian influenza in poultry," Emerg. Infect. Dis. (2006) 12:1319-1324.

(56) References Cited

OTHER PUBLICATIONS

Charbit, A. et al., "Probing the topology of a bacterial membrane protein by genetic insertion of a foreign epitope; expression at the cell surface," EMBO J (1986) 5(11):3029-3037.
Charbit, A. et al., "Versatility of a vector for expressing foreign polypeptides at the surface of gram-negative bacteria," Gene (1988) 70(1):181-189.
Chatfield et al., "The development of oral vaccines based on live attenuated *Salmonella* strains," FEMS Immunol. Med. Microbiol. (1993) 7:1-7.
Cole, K. et al., "Evaluation of a novel recombinant *Salmonella* vaccine vector for avian influenza," Poultry Science (2007) 86(Supp. 1):585-586.
Cox, M.M. et al., "Scarless and site-directed mutagenesis in *Salmonella enteritidis* chromosome," BMC Biotech. (2007) 7(59):10 pages.
Crawford, J. et al., "Baculovirus-derived hemagglutinin vaccines protect against lethal influenza infections by avian H5 and H7 subtypes," Vaccine (1999) 17:2265-2274.
De Filette, M. et al, "The universal influenza vaccine M2e-HBc administered intranasally in combination with the adjuvant CTA1-DD provides complete protection," Vaccine (2006) 24:544-551.
De Filette, M. et al., "Universal influenza A vaccine: Optimization of M2-based constructs," Virology (2005) 337:149-161.
De Filette, M. et al., "Improved design and intranasal delivery of an M2e-based human influenza A vaccine," Vaccine (2006) 24:6597-6601.
Dumitriu, I.E. et al., "HMGB1: guiding immunity from within," Trends Immunol. (2005) 26(7):381-387.
Ellis, R.W., "New technologies for making vaccines," (1988) Vaccines, Chapter 29:568-574.
Ernst, W.A. et al., "Protection against H1, H5, H6 and H9 influenza A infection with liposomal matrix 2 epitope vaccines," Vaccine (2006) 24:5158-5168.
Faham, A. et al., "Liposomal Ag engrafted with peptides of sequence derived from HMGB1 induce potent Ag-specific and anti-tumour immunity," (2009) 27(42):5846-5854.
Fan, J. et al., "Preclinical study of influenza virus A M2 peptide conjugate vaccines in mice, ferrets and rhesus monkeys," Vaccine (2004) 22:2993-3003.
Farnell, M.B. et al., "Upregulation of oxidative burst and degranulation in chicken heterophils stimulated with probiotic bacteria," Poult. Sci. (2006) 85:1900-1906.
Fecteau, J.F. et al., "CD40 Stimulation of Human Peripheral B Lymphocytes: Distinct Response from Naïve and Memory Cells," J Immunol (2003) 171:4621-4629.
Fernandez-Cabezudo et al., "Evidence for the requirement for CD40-CD154 interactions in resistance to infections with attenuated *Salmonella*," J. Endotoxin Res. (2005) 11:395-399.
Fiers, W. et al., "A universal human influenza A vaccine," Virus Research (2004) 103:173-176.
Frace, A.M. et al., "Modified M2 proteins produce heterotypic immunity against influenza A virus," Vaccine (1999) 17:2237-2244.
Gao, w. et al., "Protection of mice and poultry from lethal H5N1 avian influenza virus through adenovirus-based immunization," J. Virol. (2006) 80:1959-1964.
Gares, S.L. et al., "Immunotargeting with CD154 (CD40 ligand) enhances DNA vaccine responses in ducks," Clin. Vaccine Immun. (2006) 13:958-965.
Gast, R.K. et al., "The relationship between the magnitude of the specific antibody response to experimental *Salmonella enteritidis* infection in laying hens and their production of contaminated eggs," Avian Diseases (2001) 45:425-431.
GenBank AAQ77437, "matrix protein 2, partial [Influenza A virus (A/chicken/Chile/4957/02(H7N3))]," Mar. 3, 2004.
GenBank AF178849, "High mobility group protein HMG1 [Gallus gallus]," Sep. 27, 2000.
GenBank ABW06338, "Matrix protein 2, partial [Influenza A virus (A/Indonesia/195H/2005(H5N1))]," May 1, 2008.
GenBank ACD37491, Matrix protein 2, partial [Influenza A virus (A/Brisbane/59/2007(H1N1))], May 2008.
GenBank AAD52670, "High mobility group protein HMG1 [Gallus gallus]," Sep. 27, 2000.
Greenspan, N.S. et al., "Defining epitopes: It's not as easy as it seems," Nature Biotechnol. (1999) 17:936-937.
Grewal, I.S. et al., "CD40 and CD154 in cell-mediated immunity," Annu. Rev. Immunology. (1998) 16:111-35.
Harcourt, J.L. et al., "CD40 ligand (CD154) improves the durability of respiratory syncytial virus DNA vaccination in BALB/c mice," Vaccine (2003) 21(21-22):2964-2979.
Hargis, B, "Live Recombinant *Salmonella* Vaccination with Novel Universal Antigen Presentation and Immune Protection," USDA Grant Project Status, Jan. 14, 2012.
Harris, H.E., et al., "Mini-review: The nuclear protein HMGB1 as a proinflammatory mediator," (2004) European J. of Immunology 34:1503-1512.
Heinen, P.P. et al., "Vaccination of pigs with a DNA construct expressing an influenza virus M2-nucleoprotein fusion protein exacerbates disease after challenge with influenza A virus," Journal of General Virology (2002) 83(8):1851-1859.
Hoang, T.H. et al., "Recombinant Bacillus subtilis Expressing the Clostridium perfringens Alpha Toxoid Is a Candidate Orally Delivered Vaccine against Necrotic Enteritis," Infection and Immunity (2008) 76(11): 5257-5265.
Internation Search Report and Written Opinion for PCT Application No. PCT/US17/30764 dated Aug. 11, 2017.
Kuroda, K. & Ueda, M. "Arming Technology in Yeast—Novel Strategy for Whole-cell Biocatalyst and Protein Engineering" 2013 Biomolecules 3(3):632-50 doi: 10.3390/biom3030632.

* cited by examiner

Figure 3
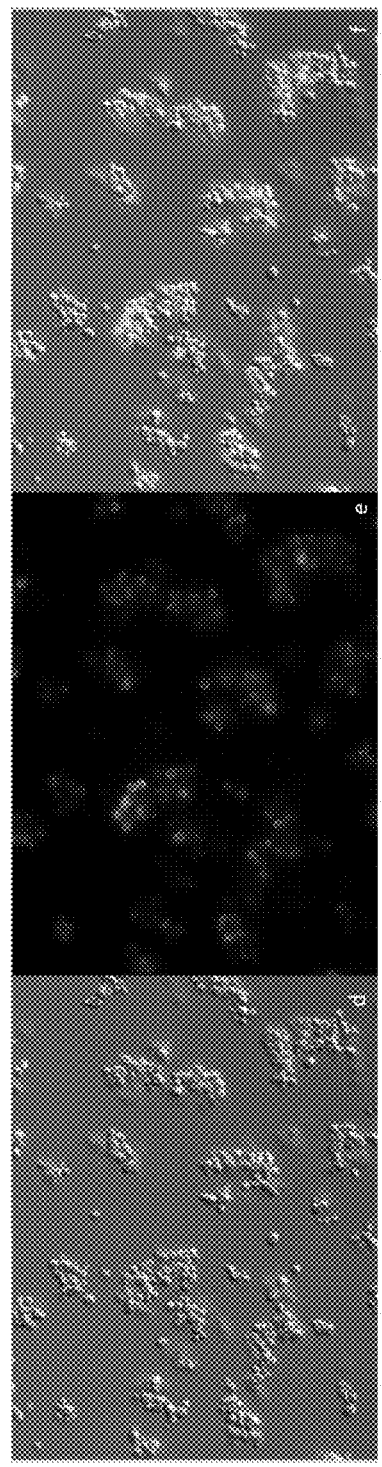

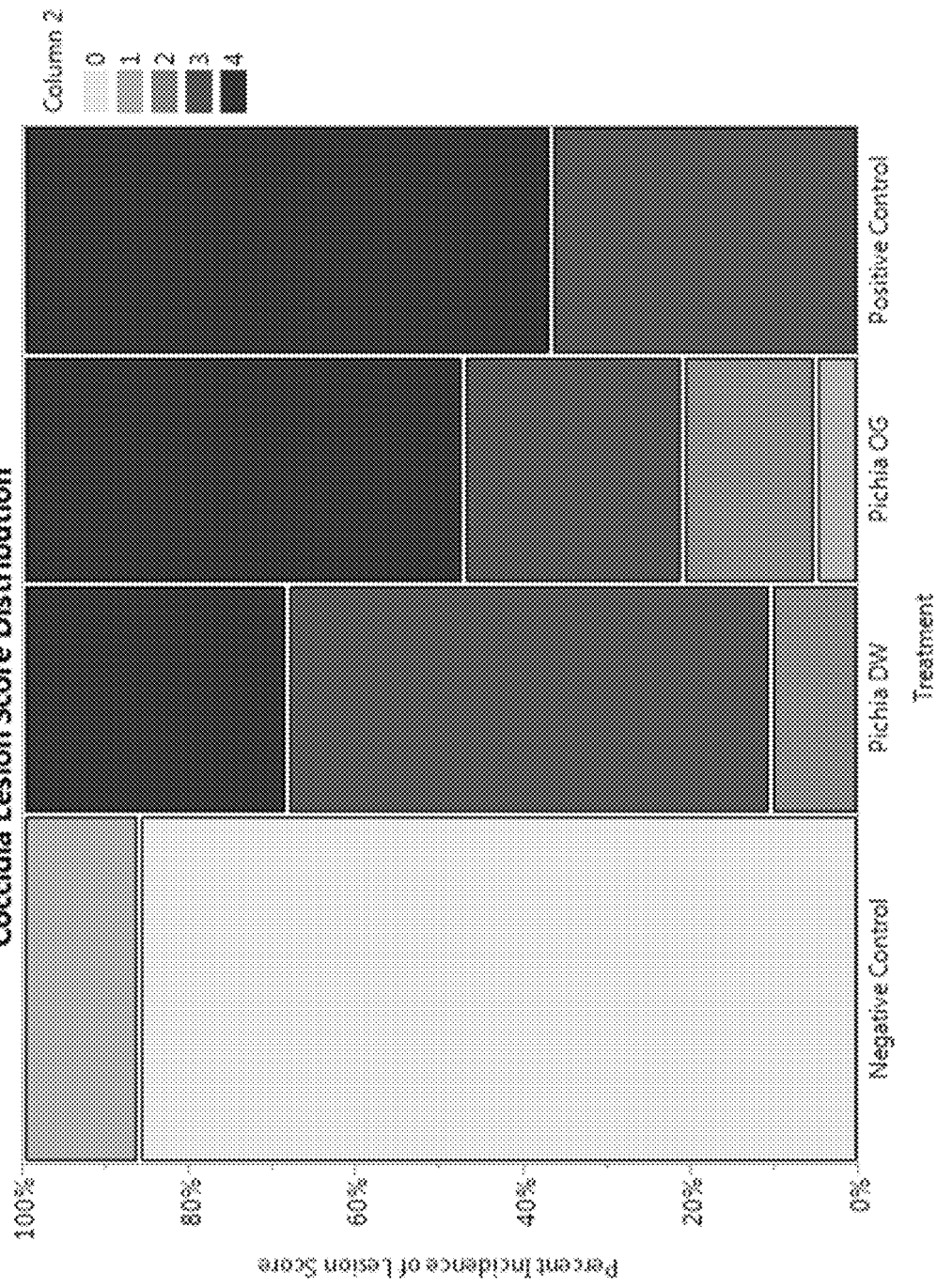

SEQUENCE LISTING

```
<160> NUMBER OF SEQ ID NOS: 129

<210> SEQ ID NO 1
<211> LENGTH: 1578
<212> TYPE: DNA
<213> ORGANISM: Saccharomyces cerevisiae
<220> FEATURE:
<221> NAME/KEY: misc_feature
<222> LOCATION: (1)..(1578)
<223> OTHER INFORMATION: HMGB1 + 3 portion of Saccharomyces cerevisiae
      alpha-agglutinin

<400> SEQUENCE: 1
cacgtgatgg gtaaaggtga tccaaaaaaa ccaagaggta aaatgtcttc ttatgctttt      60
tttgttcaaa cttgtcgtga agaacataaa aaaaaacatc cagatgcttc tgttaatttt     120
tctgaatttt ctaaaaaatg ttctgaaaga tggaaaacta tgtcttctaa agaaaaaggt     180
aaatttgaag atatggctaa agctgataaa ctacgttatg aaaaagaaat gaaaaattat     240
gttccaccaa aaggtgaaac taaaaaaaaa tttaaagatc caaatgctcc aaaaagacca     300
ccatctgctt tttttctatt ttgttctgaa tttagaccaa aaattaaagg tgaacatcca     360
ggtttatcta ttggtgatgt tgctaaaaaa ttaggtgaaa tgtggaataa tactgctgct     420
gatgataaac aaccatatga aaaaaaagct gctaaattaa agaaaaaata tgaaaaagat     480
attgctgctt atagagctaa aggtaaagtt gatgctggta aaaaagttgt tgctaaagct     540
gaaaaatcta aaaaaaaaaa agaagaagaa gaagattcct cctccggtcg gaacctcggt     600
acagctagcg ccaaaagctc ttttatctca accactacta ctgatttaac aagtataaac     660
actagtgcgt attccactgg atccattacc acagtagaaa caggcaatcg aactacatca     720
gaagtgatca gccatgtggt gactaccagc acaaaactgt ctccaactgc tactaccagc     780
ctgacaattg cacaaaccag tatctattct actgactcaa atatcacagt aggaacagat     840
```

```
attcacacca catcagaagt gattagtgat gtggaaacca ttagcagaga aacagcttcg    900
accgttgtag ccgctccaac ctcaacaact ggatggacag gcgctatgaa tacttacatc    960
tcgcaattta catcctcttc tttcgcaaca atcaacagca caccaataat ctcttcatca   1020
gcagtatttg aaacctcaga tgcttcaatt gtcaatgtgc acactgaaaa tatcacgaat   1080
actgctgctg ttccatctga agagcccact tttgtaaatg ccacgagaaa ctccttaaat   1140
tccttctgca gcagcaaaca gccatccagt ccctcatctt atacgtcttc cccactcgta   1200
tcgtccctct ccgtaagcaa aacattacta agcaccagtt ttacgccttc tgtgccaaca   1260
tctaatacat atatcaaaac gaaaaatacg ggttactttg agcacacggc tttgacaaca   1320
tcttcagttg gccttaattc ttttagtgaa acagcagtct catctcaggg aacgaaaatt   1380
gacacctttt tagtgtcatc cttgatcgca tatccttctt ctgcatcagg aagccaattg   1440
tccggtatcc aacagaattt cacatcaact tctctcatga tttcaaccta tgaaggtaaa   1500
gcgtctatat ttttctcagc tgagctcggt tcgatcattt ttctgctttt gtcgtacctg   1560
ctattctaat aaggtacc                                                 1578

<210> SEQ ID NO 2
<211> LENGTH: 215
<212> TYPE: PRT
<213> ORGANISM: Gallus gallus
<220> FEATURE:
<221> NAME/KEY: misc_feature
<222> LOCATION: (1)..(215)
<223> OTHER INFORMATION: HMGB1

<400> SEQUENCE: 2

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Phe Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Asp Glu Asp
            180                 185                 190

Glu Asp Glu Glu Asp Glu Glu Asp Glu Glu Glu Glu Glu Glu
        195                 200                 205

Glu Asp Asp Asp Asp Asp Glu
```

210             215

<210> SEQ ID NO 3
<211> LENGTH: 205
<212> TYPE: PRT
<213> ORGANISM: Danio rerio
<220> FEATURE:
<221> NAME/KEY: misc_feature
<222> LOCATION: (1)..(205)
<223> OTHER INFORMATION: HMGB1

<400> SEQUENCE: 3

Met Gly Lys Asp Pro Thr Lys Pro Arg Gly Lys Met Ser Ser Tyr Ala
1               5                   10                  15

Tyr Phe Val Gln Thr Cys Arg Glu Glu His Lys Lys His Pro Glu
            20                  25                  30

Ala Thr Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Leu Asp Lys Ala Arg Tyr Glu Arg Glu Met Lys Asn Tyr Ile Pro Pro
65                  70                  75                  80

Lys Gly Glu Lys Lys Lys Arg Phe Lys Asp Pro Asn Ala Pro Lys Arg
                85                  90                  95

Pro Pro Ser Ala Phe Phe Ile Phe Cys Ser Glu Phe Arg Pro Lys Val
            100                 105                 110

Lys Glu Glu Thr Pro Gly Leu Ser Ile Gly Asp Val Ala Lys Arg Leu
        115                 120                 125

Gly Glu Met Trp Asn Lys Ile Ser Ser Glu Glu Lys Gln Pro Tyr Glu
    130                 135                 140

Lys Lys Ala Ala Lys Leu Lys Glu Lys Tyr Glu Lys Asp Ile Ala Ala
145                 150                 155                 160

Tyr Arg Ser Lys Gly Lys Val Gly Gly Ala Ala Lys Ala Pro Ser
                165                 170                 175

Lys Pro Asp Lys Ala Asn Asp Glu Asp Glu Asp Asp Glu Glu Glu
            180                 185                 190

Asp Glu Asp Asp Asp Asp Glu Glu Glu Asp Asp Glu
        195                 200                 205

<210> SEQ ID NO 4
<211> LENGTH: 215
<212> TYPE: PRT
<213> ORGANISM: Homo sapiens
<220> FEATURE:
<221> NAME/KEY: misc_feature
<222> LOCATION: (1)..(215)
<223> OTHER INFORMATION: HMGB1

<400> SEQUENCE: 4

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
        85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215

<210> SEQ ID NO 5
<211> LENGTH: 215
<212> TYPE: PRT
<213> ORGANISM: Mus musculus
<220> FEATURE:
<221> NAME/KEY: misc_feature
<222> LOCATION: (1)..(215)
<223> OTHER INFORMATION: HMGB1

<400> SEQUENCE: 5

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
            85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Glu Glu Asp Glu Asp Glu
        195                 200                 205

```
Glu Glu Asp Asp Asp Asp Glu
    210             215

<210> SEQ ID NO 6
<211> LENGTH: 215
<212> TYPE: PRT
<213> ORGANISM: Rattus norvegicus
<220> FEATURE:
<221> NAME/KEY: misc_feature
<222> LOCATION: (1)..(215)
<223> OTHER INFORMATION: HMGB1

<400> SEQUENCE: 6

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Asp Asp Glu Glu
            180                 185                 190

Asp Glu Glu Asp Glu Glu Glu Glu Glu Glu Asp Glu Asp Glu
        195                 200                 205

Glu Glu Asp Asp Asp Asp Glu
    210             215

<210> SEQ ID NO 7
<211> LENGTH: 180
<212> TYPE: PRT
<213> ORGANISM: Cricetulus griseus
<220> FEATURE:
<221> NAME/KEY: misc_feature
<222> LOCATION: (1)..(180)
<223> OTHER INFORMATION: HMGB1

<400> SEQUENCE: 7

Val Asn Phe Ser Glu Phe Ser Lys Lys Cys Ser Glu Arg Trp Lys Thr
1               5                   10                  15

Met Ser Ala Lys Glu Lys Gly Lys Phe Glu Asp Met Ala Lys Ala Asp
                20                  25                  30

Lys Ala Arg Tyr Glu Arg Glu Met Lys Thr Tyr Ile Pro Pro Lys Gly
            35                  40                  45

Glu Thr Lys Lys Lys Phe Lys Asp Pro Asn Ala Pro Lys Arg Pro Pro
```

```
                50                  55                  60
Ser Ala Phe Phe Leu Phe Cys Ser Glu Tyr Arg Pro Lys Ile Lys Gly
 65                  70                  75                  80

Glu His Pro Gly Leu Ser Ile Gly Asp Val Ala Lys Lys Leu Gly Glu
                 85                  90                  95

Met Trp Asn Asn Thr Ala Ala Asp Asp Lys Gln Pro Tyr Glu Lys Lys
                100                 105                 110

Ala Ala Lys Leu Lys Glu Lys Tyr Glu Lys Asp Ile Ala Ala Tyr Arg
            115                 120                 125

Ala Lys Gly Lys Pro Asp Ala Ala Lys Lys Gly Val Val Lys Ala Glu
            130                 135                 140

Lys Ser Lys Lys Lys Lys Glu Glu Glu Asp Asp Glu Glu Asp Glu Glu
145                 150                 155                 160

Asp Glu Glu Glu Glu Glu Glu Glu Asp Glu Asp Glu Glu Glu Glu Asp
                165                 170                 175

Asp Asp Asp Glu
            180

<210> SEQ ID NO 8
<211> LENGTH: 215
<212> TYPE: PRT
<213> ORGANISM: Macaca mulatta
<220> FEATURE:
<221> NAME/KEY: misc_feature
<222> LOCATION: (1)..(215)
<223> OTHER INFORMATION: HMGB1

<400> SEQUENCE: 8

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
            130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
            195                 200                 205

Glu Glu Asp Asp Asp Asp Glu
            210                 215
```

<210> SEQ ID NO 9
<211> LENGTH: 215
<212> TYPE: PRT
<213> ORGANISM: Macaca fascicularis
<220> FEATURE:
<221> NAME/KEY: misc_feature
<222> LOCATION: (1)..(215)
<223> OTHER INFORMATION: HMGB1

<400> SEQUENCE: 9

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Asp Glu Asp Glu Asp Glu
        195                 200                 205

Glu Glu Asp Asp Asp Asp Glu
    210                 215
```

<210> SEQ ID NO 10
<211> LENGTH: 227
<212> TYPE: PRT
<213> ORGANISM: Otolemur garnettii
<220> FEATURE:
<221> NAME/KEY: misc_feature
<222> LOCATION: (1)..(227)
<223> OTHER INFORMATION: HMGB1

<400> SEQUENCE: 10

```
Met Asp Lys Gly Asp Pro Lys Lys Pro Arg Gly Lys Met Ser Ser Cys
1               5                   10                  15

Ala Phe Phe Val Gln Thr Cys Arg Gly Glu Glu Arg Glu Lys Lys His
            20                  25                  30

Pro Asp Ala Ser Val Asn Phe Ser Glu Phe Ser Lys Lys Cys Ser Glu
        35                  40                  45

Arg Trp Lys Thr Met Ser Ala Lys Glu Lys Gly Lys Phe Glu Asp Met
    50                  55                  60
```

```
Ala Lys Ala Asp Lys Ala Arg Tyr Glu Arg Glu Met Lys Thr Tyr Ile
 65                  70                  75                  80

Pro Pro Lys Gly Glu Thr Lys Lys Lys Phe Lys Asp Pro Asn Ala Pro
                 85                  90                  95

Lys Arg Pro Pro Ser Ala Phe Phe Leu Phe Cys Ser Glu Tyr Arg Pro
            100                 105                 110

Lys Ile Lys Gly Glu His His Leu Ser Thr Gly Asp Val Ala Lys Lys
        115                 120                 125

Leu Gly Glu Met Trp Ser Asn Pro Ala Ala Gly Asp Lys Gln Pro Glu
    130                 135                 140

Glu Lys Lys Ala Ala Lys Leu Glu Glu Lys Asp Lys Lys Asp Ile Ala
145                 150                 155                 160

Ala Tyr Arg Ala Lys Gly Lys Pro Val Gly Ser Ser Arg Leu Lys Lys
                165                 170                 175

Ala Arg Lys Arg Arg Lys Arg Lys Met Arg Lys Met Lys Arg Lys
                180                 185                 190

Lys Met Met Asn Lys Leu Val Leu Ala Gln Phe Leu Phe Leu Val Tyr
            195                 200                 205

Lys Ala Phe Asn Pro Leu Val Tyr Asn Ser Leu Leu Leu Lys Lys Lys
    210                 215                 220

Ile Glu Met
225

<210> SEQ ID NO 11
<211> LENGTH: 211
<212> TYPE: PRT
<213> ORGANISM: Xenopus laevis
<220> FEATURE:
<221> NAME/KEY: misc_feature
<222> LOCATION: (1)..(211)
<223> OTHER INFORMATION: HMGB1

<400> SEQUENCE: 11

Met Gly Lys Gly Asp Pro Lys Lys Pro Arg Gly Lys Met Ser Ser Tyr
  1               5                  10                  15

Ala Tyr Phe Val Gln Thr Cys Arg Glu Glu His Lys Lys Lys His Pro
                 20                  25                  30

Asp Ala Ser Val Asn Phe Ala Glu Phe Ser Lys Lys Cys Ser Glu Arg
             35                  40                  45

Trp Lys Thr Met Ser Ala Lys Glu Lys Ser Lys Phe Glu Asp Met Ala
     50                  55                  60

Lys Ala Asp Lys Val Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Phe Arg Pro Lys
            100                 105                 110

Ile Lys Gly Glu His Pro Gly Ser Thr Ile Gly Asp Ile Ala Lys Lys
        115                 120                 125

Leu Gly Glu Met Trp Asn Asn Thr Ala Thr Asp Asp Lys Leu Pro Phe
    130                 135                 140

Glu Arg Lys Ala Ala Lys Leu Lys Glu Lys Tyr Glu Lys Asp Val Ala
145                 150                 155                 160

Ala Tyr Arg Ala Lys Gly Lys Pro Glu Pro Ala Lys Lys Ala Pro Ala
                165                 170                 175

Lys Pro Glu Lys Ala Lys Lys Lys Glu Glu Asp Asp Glu Asp Asp Asp
```

```
                    180                 185                 190
Glu Glu Asp Glu Asp Glu Glu Asp Glu Glu Glu Glu Glu Glu Asp
                195                 200                 205

Asp Asp Glu
        210

<210> SEQ ID NO 12
<211> LENGTH: 211
<212> TYPE: PRT
<213> ORGANISM: Xenopus (Silurana) tropicalis
<220> FEATURE:
<221> NAME/KEY: misc_feature
<222> LOCATION: (1)..(211)
<223> OTHER INFORMATION: HMGB1

<400> SEQUENCE: 12

Met Gly Lys Gly Asp Pro Lys Lys Pro Arg Gly Lys Met Ser Ser Tyr
1               5                   10                  15

Ala Tyr Phe Val Gln Thr Cys Arg Glu Glu His Lys Lys Lys His Pro
            20                  25                  30

Asp Ala Ser Val Asn Phe Ala Glu Phe Ser Lys Lys Cys Ser Glu Arg
        35                  40                  45

Trp Lys Thr Met Ser Ala Lys Glu Ser Lys Phe Glu Asp Met Ala
    50                  55                  60

Lys Ala Asp Lys Val Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Phe Arg Pro Lys
                100                 105                 110

Ile Lys Gly Glu His Pro Gly Ser Thr Ile Gly Asp Ile Ala Lys Lys
                115                 120                 125

Leu Gly Glu Met Trp Asn Asn Thr Ala Thr Asp Asp Lys Leu Pro Tyr
            130                 135                 140

Glu Arg Lys Ala Ala Lys Leu Lys Glu Lys Tyr Glu Lys Asp Val Ala
145                 150                 155                 160

Ala Tyr Arg Ala Lys Gly Lys Pro Glu Pro Ala Lys Lys Ala Pro Ala
                165                 170                 175

Lys Phe Glu Lys Ala Lys Lys Lys Glu Asp Asp Asp Asp Glu Asp
                180                 185                 190

Asp Asp Asp Glu Glu Glu Glu Asp Glu Glu Glu Glu Asp Glu Glu Asp
                195                 200                 205

Asp Asp Glu
        210

<210> SEQ ID NO 13
<211> LENGTH: 215
<212> TYPE: PRT
<213> ORGANISM: Papio Anubis
<220> FEATURE:
<221> NAME/KEY: misc_feature
<222> LOCATION: (1)..(215)
<223> OTHER INFORMATION: HMGB1

<400> SEQUENCE: 13

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30
```

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
                180                 185                 190

Asp Glu Glu Asp Glu Glu Glu Glu Asp Glu Glu Asp Glu Asp Glu
                195                 200                 205

Glu Glu Asp Asp Asp Asp Glu
                210                 215

<210> SEQ ID NO 14
<211> LENGTH: 215
<212> TYPE: PRT
<213> ORGANISM: Callicebus moloch
<220> FEATURE:
<221> NAME/KEY: misc_feature
<222> LOCATION: (1)..(215)
<223> OTHER INFORMATION: HMGB1

<400> SEQUENCE: 14

Met Gly Lys Gly Asp Pro Lys Lys Pro Arg Gly Lys Met Ser Ser Tyr
  1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

```
Ala Tyr Arg Ala Lys Gly Lys Pro Asp Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215

<210> SEQ ID NO 15
<211> LENGTH: 215
<212> TYPE: PRT
<213> ORGANISM: Callithrix jacchus
<220> FEATURE:
<221> NAME/KEY: misc_feature
<222> LOCATION: (1)..(215)
<223> OTHER INFORMATION: HMGB1

<400> SEQUENCE: 15

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215

<210> SEQ ID NO 16
<211> LENGTH: 215
<212> TYPE: PRT
<213> ORGANISM: Bos taurus
<220> FEATURE:
<221> NAME/KEY: misc_feature
<222> LOCATION: (1)..(215)
<223> OTHER INFORMATION: HMGB1

<400> SEQUENCE: 16

Met Gly Lys Gly Asp Pro Lys Lys Pro Arg Gly Lys Met Ser Ser Tyr
```

```
            1               5                  10                 15
        Ala Phe Phe Val Gln Thr Cys Arg Glu Glu His Lys Lys Lys His Pro
                         20                  25                 30

Asp Ala Ser Val Asn Phe Ser Glu Phe Ser Lys Lys Cys Ser Glu Arg
                         35                  40                 45

Trp Lys Thr Met Ser Ala Lys Glu Lys Gly Lys Phe Glu Asp Met Ala
                         50                  55                 60

Lys Ala Asp Lys Ala Arg Tyr Glu Arg Glu Met Lys Thr Tyr Ile Pro
         65                  70                  75                 80

Pro Lys Gly Glu Thr Lys Lys Lys Phe Lys Asp Pro Asn Ala Pro Lys
                         85                  90                 95

Arg Pro Pro Ser Ala Phe Phe Leu Phe Cys Ser Glu Tyr Arg Pro Lys
                        100                 105                110

Ile Lys Gly Glu His Pro Gly Leu Ser Ile Gly Asp Val Ala Lys Lys
                        115                 120                125

Leu Gly Glu Met Trp Asn Asn Thr Ala Ala Asp Asp Lys Gln Pro Tyr
                        130                 135                140

Glu Lys Lys Ala Ala Lys Leu Lys Glu Lys Tyr Glu Lys Asp Ile Ala
        145                 150                 155                160

Ala Tyr Arg Ala Lys Gly Lys Pro Asp Ala Ala Lys Lys Gly Val Val
                        165                 170                175

Lys Ala Glu Lys Ser Lys Lys Lys Glu Glu Glu Glu Asp Glu Glu
                        180                 185                190

Asp Glu Glu Asp Glu Glu Glu Glu Asp Glu Glu Asp Glu Glu Glu
                        195                 200                205

Glu Glu Asp Asp Asp Asp Glu
                        210                 215

<210> SEQ ID NO 17
<211> LENGTH: 214
<212> TYPE: PRT
<213> ORGANISM: Bos indicus
<220> FEATURE:
<221> NAME/KEY: misc_feature
<222> LOCATION: (1)..(214)
<223> OTHER INFORMATION: HMGB1

<400> SEQUENCE: 17

Met Gly Lys Gly Asp Pro Lys Lys Pro Arg Gly Lys Met Ser Ser Tyr
         1                   5                  10                 15

Ala Phe Phe Val Gln Thr Cys Arg Glu Glu His Lys Lys Lys His Pro
                         20                  25                 30

Asp Ala Ser Val Asn Phe Ser Glu Phe Ser Lys Lys Cys Ser Glu Arg
                         35                  40                 45

Trp Lys Thr Met Ser Ala Lys Glu Lys Gly Lys Phe Glu Asp Met Ala
                         50                  55                 60

Lys Ala Asp Lys Ala Arg Tyr Glu Arg Glu Met Lys Thr Tyr Ile Pro
         65                  70                  75                 80

Pro Lys Gly Glu Thr Lys Lys Lys Phe Lys Asp Pro Asn Ala Pro Lys
                         85                  90                 95

Arg Pro Pro Ser Ala Phe Phe Leu Phe Cys Ser Glu Tyr Arg Pro Lys
                        100                 105                110

Ile Lys Gly Glu His Pro Gly Leu Ser Ile Gly Asp Val Ala Lys Lys
                        115                 120                125

Leu Gly Glu Met Trp Asn Asn Thr Ala Ala Asp Asp Lys Gln Pro Tyr
                        130                 135                140
```

```
Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Lys
                165                 170                 175

Ala Glu Lys Ser Lys Lys Lys Glu Glu Glu Asp Glu Glu Asp
                180                 185                 190

Glu Glu Asp Glu Glu Glu Glu Asp Glu Glu Asp Glu Glu Glu
        195                 200                 205

Glu Asp Asp Asp Asp Glu
        210
```

<210> SEQ ID NO 18
<211> LENGTH: 215
<212> TYPE: PRT
<213> ORGANISM: Equus caballus
<220> FEATURE:
<221> NAME/KEY: misc_feature
<222> LOCATION: (1)..(215)
<223> OTHER INFORMATION: HMGB1

<400> SEQUENCE: 18

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
        210                 215
```

<210> SEQ ID NO 19
<211> LENGTH: 215
<212> TYPE: PRT
<213> ORGANISM: Canis lupus familiaris
<220> FEATURE:
<221> NAME/KEY: misc_feature
<222> LOCATION: (1)..(215)
<223> OTHER INFORMATION: HMGB1

<400> SEQUENCE: 19

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
            85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
        210                 215

<210> SEQ ID NO 20
<211> LENGTH: 215
<212> TYPE: PRT
<213> ORGANISM: Sus scrofa
<220> FEATURE:
<221> NAME/KEY: misc_feature
<222> LOCATION: (1)..(215)
<223> OTHER INFORMATION: HMGB1

<400> SEQUENCE: 20

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
            85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys

```
            115                 120                 125
Leu Gly Glu Met Trp Asn Asn Thr Ala Ala Asp Asp Lys His Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
                180                 185                 190

Asp Glu Glu Asp Glu Glu Glu Glu Asp Glu Glu Asp Glu Glu Glu
            195                 200                 205

Glu Glu Asp Asp Asp Asp Glu
        210                 215

<210> SEQ ID NO 21
<211> LENGTH: 215
<212> TYPE: PRT
<213> ORGANISM: Oryctolagus cuniculus
<220> FEATURE:
<221> NAME/KEY: misc_feature
<222> LOCATION: (1)..(215)
<223> OTHER INFORMATION: HMGB1

<400> SEQUENCE: 21

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
                180                 185                 190

Asp Glu Glu Asp Glu Glu Glu Glu Asp Glu Glu Asp Glu Asp Glu
            195                 200                 205

Glu Glu Asp Asp Asp Asp Glu
        210                 215

<210> SEQ ID NO 22
<211> LENGTH: 206
<212> TYPE: PRT
<213> ORGANISM: Sciaenops ocellatus
```

```
<220> FEATURE:
<221> NAME/KEY: misc_feature
<222> LOCATION: (1)..(206)
<223> OTHER INFORMATION: HMGB1

<400> SEQUENCE: 22
```

Met Val Lys Glu Gln Gly Lys Pro Arg Gly Lys Met Ser Ser Tyr Ala
1               5                   10                  15

Tyr Phe Val Gln Thr Cys Arg Glu Glu His Lys Lys Lys His Pro Asp
            20                  25                  30

Ala Ser Val Asn Phe Ala Glu Phe Ser Lys Lys Cys Ser Gly Arg Trp
        35                  40                  45

Lys Thr Met Ser Ser Lys Glu Lys Gly Lys Phe Glu Asp Leu Ala Arg
    50                  55                  60

Gln Asp Lys Ala Arg Tyr Glu Arg Glu Met Met Ser Tyr Val Pro Ala
65                  70                  75                  80

Arg Gly Gly Lys Lys Lys Lys Tyr Lys Asp Pro Asn Ala Pro Lys Arg
                85                  90                  95

Pro Pro Ser Ala Phe Phe Ile Phe Cys Ser Glu Phe Arg Pro Lys Val
            100                 105                 110

Lys Gly Glu Ala Pro Gly Leu Thr Ile Gly Glu Val Ala Lys Arg Leu
        115                 120                 125

Gly Glu Met Trp Asn Gly Thr Ala Ser Glu Asp Lys Gln Pro Phe Glu
130                 135                 140

Lys Lys Ala Ala Lys Leu Lys Glu Lys Tyr Glu Lys Glu Val Ala Ala
145                 150                 155                 160

Tyr Arg Gln Lys Thr Lys Ala Gly Ala Gly Pro Ala Ala Lys Ala Pro
                165                 170                 175

Ala Lys Val Glu Lys Lys Val Glu Asp Asp Asp Asp Asp Asp Asp Asp
            180                 185                 190

Asp Glu Glu Glu Glu Glu Asp Asp Tyr Asp Asp Asp Glu
        195                 200                 205

```
<210> SEQ ID NO 23
<211> LENGTH: 182
<212> TYPE: PRT
<213> ORGANISM: Ictalurus punctatus
<220> FEATURE:
<221> NAME/KEY: misc_feature
<222> LOCATION: (1)..(182)
<223> OTHER INFORMATION: HMGB1

<400> SEQUENCE: 23
```

Gln Thr Cys Arg Glu Glu His Lys Lys Lys His Pro Asp Thr Ser Val
1               5                   10                  15

Asn Phe Ser Glu Phe Ser Lys Lys Cys Ser Glu Arg Trp Lys Thr Met
            20                  25                  30

Ser Ala Lys Glu Lys Gly Lys Phe Glu Asp Met Ala Arg Leu Asp Lys
        35                  40                  45

Ala Arg Tyr Glu Arg Glu Met Lys Asn Tyr Val Pro Pro Arg Gly Glu
    50                  55                  60

Lys Lys Lys Arg Phe Lys Asp Pro Asn Ala Pro Lys Arg Pro Pro Ser
65                  70                  75                  80

Ala Phe Phe Ile Phe Cys Ala Glu Tyr Arg Pro Lys Val Lys Glu Glu
                85                  90                  95

Thr Pro Gly Leu Ser Ile Gly Asp Val Ala Lys Lys Leu Gly Glu Met
            100                 105                 110

Trp Asn Lys Thr Ser Ala Glu Glu Lys Gln Pro Tyr Glu Lys Lys Ala
            115                 120                 125

Ala Lys Leu Lys Glu Lys Tyr Glu Lys Asp Ile Ala Ala Tyr Arg Lys
130                 135                 140

Gly Lys Val Val Gly Gly Ala Ala Lys Ala Pro Thr Lys Pro Asp Lys
145                 150                 155                 160

Ala Asp Asp Asp Glu Asp Asp Asp Asp Glu Asp Asp Asp Asp
            165                 170                 175

Asp Asp Glu Asp Asp Glu
            180

<210> SEQ ID NO 24
<211> LENGTH: 209
<212> TYPE: PRT
<213> ORGANISM: Lutjanus sanguineus
<220> FEATURE:
<221> NAME/KEY: misc_feature
<222> LOCATION: (1)..(209)
<223> OTHER INFORMATION: HMGB1

<400> SEQUENCE: 24

Met Gly Arg Glu Pro Arg Glu Pro Gly Lys Pro Arg Gly Lys Met Ser
1               5                   10                  15

Ser Tyr Ala Tyr Phe Val Gln Thr Cys Arg Glu Glu His Lys Lys Lys
                20                  25                  30

His Pro Asp Ala Ser Val Asn Phe Ala Glu Phe Ser Lys Lys Cys Ser
            35                  40                  45

Glu Arg Trp Lys Thr Met Ser Pro Lys Glu Lys Ser Lys Phe Glu Asp
    50                  55                  60

Leu Ala Arg Gln Asp Lys Ala Arg Tyr Glu Arg Glu Met Leu Thr Tyr
65                  70                  75                  80

Val Pro Ala Arg Gly Gly Lys Lys Lys Phe Lys Asp Pro Asn Ala
                85                  90                  95

Pro Lys Arg Pro Pro Ser Ala Phe Phe Ile Phe Cys Ser Glu Phe Arg
            100                 105                 110

Pro Lys Val Lys Gly Glu Ser Pro Gly Leu Ser Ile Gly Glu Val Ala
            115                 120                 125

Lys Arg Leu Gly Glu Met Trp Asn Gly Thr Ser Ser Glu Asp Lys Gln
130                 135                 140

Pro Phe Glu Lys Lys Ala Ala Lys Leu Lys Glu Arg Tyr Glu Lys Glu
145                 150                 155                 160

Val Ala Ala Tyr Arg Gln Lys Thr Lys Gly Gly Ser Ala Pro Ala Gly
                165                 170                 175

Lys Ala Pro Ala Lys Ala Glu Lys Lys Val Glu Glu Asp Asp Asp Asp
            180                 185                 190

Glu Glu Asp Asp Asp Asp Glu Glu Glu Asp Tyr Asp Asp Asp Asp
            195                 200                 205

Glu

<210> SEQ ID NO 25
<211> LENGTH: 204
<212> TYPE: PRT
<213> ORGANISM: Carassius auratus
<220> FEATURE:
<221> NAME/KEY: misc_feature
<222> LOCATION: (1)..(204)
<223> OTHER INFORMATION: HMGB1

<400> SEQUENCE: 25

```
Met Gly Lys Asp Pro Thr Lys Pro Arg Gly Lys Met Ser Ser Tyr Ala
1               5                   10                  15

Tyr Phe Val Gln Thr Cys Arg Glu Glu His Lys Lys Lys His Pro Glu
            20                  25                  30

Ala Thr Val Asn Phe Ser Glu Phe Ser Lys Lys Cys Ser Glu Arg Trp
            35                  40                  45

Lys Thr Met Ser Gly Lys Glu Lys Gly Lys Phe Glu Asp Met Ala Lys
50                  55                  60

Gln Asp Lys Val Arg Tyr Glu Arg Glu Met Lys Asn Tyr Ile Pro Pro
65                  70                  75                  80

Lys Gly Glu Lys Lys Arg Phe Lys Asp Pro Asn Ala Pro Lys Arg
                85                  90                  95

Pro Pro Ser Ala Phe Phe Ile Phe Cys Ser Glu Phe Arg Ser Lys Val
            100                 105                 110

Lys Glu Glu Thr Pro Gly Leu Ser Ile Gly Asp Val Ala Lys Arg Leu
            115                 120                 125

Gly Glu Met Trp Asn Lys Thr Ser Ala Glu Asp Lys Gln Pro Phe Glu
            130                 135                 140

Lys Lys Ala Ala Lys Leu Lys Glu Lys Tyr Glu Lys Asp Ile Ala Ala
145                 150                 155                 160

Tyr Arg Ser Lys Gly Lys Val Val Gly Ala Ala Lys Ala Pro Ser
                165                 170                 175

Lys Pro Val Lys Val Asn Asp Asp Asp Asp Asp Glu Asp Glu
            180                 185                 190

Asp Glu Asp Asp Asp Glu Glu Asp Asp Glu
            195                 200

<210> SEQ ID NO 26
<211> LENGTH: 198
<212> TYPE: PRT
<213> ORGANISM: Salmo salar
<220> FEATURE:
<221> NAME/KEY: misc_feature
<222> LOCATION: (1)..(198)
<223> OTHER INFORMATION: HMGB1

<400> SEQUENCE: 26

Met Gly Lys Asp Pro Arg Lys Pro Arg Gly Lys Met Ser Ser Tyr Ala
1               5                   10                  15

Tyr Phe Val Gln Thr Cys Arg Glu Glu His Lys Lys Lys His Pro Glu
            20                  25                  30

Ala Ser Val Asn Phe Ser Glu Phe Ser Lys Lys Cys Ser Glu Arg Trp
            35                  40                  45

Arg Thr Met Ser Ala Lys Glu Lys Gly Lys Phe Glu Asp Leu Ala Lys
50                  55                  60

Leu Asp Lys Val Arg Tyr Glu Arg Glu Met Arg Ser Tyr Ile Pro Pro
65                  70                  75                  80

Lys Gly Glu Lys Lys Lys Arg Phe Lys Asp Pro Asn Ala Pro Lys Arg
                85                  90                  95

Pro Ser Ser Ala Phe Phe Ile Phe Cys Ala Asp Phe Arg Pro Gln Val
            100                 105                 110

Lys Gly Glu Thr Pro Gly Leu Ser Ile Gly Asp Val Ala Lys Lys Leu
            115                 120                 125

Gly Glu Lys Trp Asn Asn Leu Thr Ala Glu Asp Lys Val Pro Tyr Glu
            130                 135                 140
```

```
Lys Lys Ala Ala Lys Leu Lys Glu Lys Tyr Glu Lys Asp Ile Thr Ala
145                 150                 155                 160

Tyr Arg Asn Lys Gly Lys Val Pro Val Ser Val Pro Lys Ala Ala
                165                 170                 175

Ala Pro Thr Lys Asp Asp Asp Asp Asp Asp Asp Asp Asp Asp
            180                 185                 190

Glu Asp Asp Asp Asp Asp
            195

<210> SEQ ID NO 27
<211> LENGTH: 206
<212> TYPE: PRT
<213> ORGANISM: Anoplopoma fimbria
<220> FEATURE:
<221> NAME/KEY: misc_feature
<222> LOCATION: (1)..(206)
<223> OTHER INFORMATION: HMGB1

<400> SEQUENCE: 27

Met Val Lys Glu Leu Gly Lys Pro Lys Gly Lys Met Ser Ser Tyr Ala
1               5                   10                  15

Tyr Phe Val Gln Thr Cys Arg Glu Glu His Lys Lys Lys His Pro Glu
            20                  25                  30

Ala Ser Val Asn Phe Ser Glu Phe Ser Lys Lys Cys Ser Glu Arg Trp
        35                  40                  45

Lys Thr Met Ser Leu Lys Glu Gly Lys Phe Glu Asp Leu Ala Arg
    50                  55                  60

Gln Asp Lys Ala Arg Tyr Glu Arg Glu Met Met Ser Tyr Ile Pro Pro
65                  70                  75                  80

Arg Gly Ile Lys Lys Lys Lys Phe Lys Asp Pro Asn Ala Pro Lys Arg
                85                  90                  95

Pro Pro Ser Ala Phe Phe Ile Phe Cys Ala Glu Tyr Arg Pro Lys Val
            100                 105                 110

Lys Gly Glu Thr Pro Gly Ala Thr Ile Gly Asp Val Ala Lys Arg Leu
        115                 120                 125

Gly Glu Met Trp Asn Gly Thr Ala Ser Glu Asp Arg Gln Pro Phe Glu
130                 135                 140

Lys Lys Ala Ala Lys Leu Lys Glu Lys Tyr Glu Lys Glu Val Ala Ala
145                 150                 155                 160

Tyr Arg Ala Lys Thr Lys Pro Gly Ala Cys Ala Ala Ala Pro Ser
            165                 170                 175

Lys Ala Pro Ala Lys Val Glu Lys Val Glu Asp Asp Asp Asp
        180                 185                 190

Asp Asp Asp Glu Glu Glu Asp Asp Phe Asp Asp Asp Asp Asp
            195                 200                 205

<210> SEQ ID NO 28
<211> LENGTH: 194
<212> TYPE: PRT
<213> ORGANISM: Oncorhynchus mykiss
<220> FEATURE:
<221> NAME/KEY: misc_feature
<222> LOCATION: (1)..(194)
<223> OTHER INFORMATION: HMGB1

<400> SEQUENCE: 28

Met Gly Lys Asp Pro Arg Lys Pro Arg Gly Lys Met Ser Ser Tyr Ala
1               5                   10                  15

Tyr Phe Val Gln Thr Cys Arg Ala Glu His Lys Lys Lys His Pro Glu
```

```
            20                  25                  30
Ala Ser Val Asn Phe Ala Glu Phe Ser Lys Lys Cys Ser Glu Arg Trp
        35                  40                  45
Lys Pro Met Ser Pro Lys Glu Lys Gly Lys Phe Glu Asp Met Ala Lys
    50                  55                  60
Gln Asp Lys Val Arg Tyr Glu Gly Glu Met Lys Asn Tyr Ile Pro Pro
65                  70                  75                  80
Asn Gly Gln Lys Lys Lys Arg Phe Lys Asp Pro Asn Ala Pro Lys Arg
                85                  90                  95
Pro Pro Ser Ala Phe Phe Ile Phe Cys Ala Asp Phe Arg Ala Lys Ile
            100                 105                 110
Lys Ser Glu His Pro Gly Leu Ser Ile Gly Asp Thr Ala Lys Lys Leu
        115                 120                 125
Gly Val Met Trp Asn Ser Ala Ala Glu Lys Lys Pro Tyr Glu
    130                 135                 140
Lys Lys Ala Ala Thr Leu Lys Glu Lys Tyr Asp Lys Asp Ile Ala Ser
145                 150                 155                 160
Tyr Arg Thr Asn Gly Arg Val Asp Thr Ala Ser Ser Ala Ala Ala Asp
                165                 170                 175
Asp Glu Glu Glu Asp Asp Glu Glu Asp Asp Glu Asp Glu Asp Asp
            180                 185                 190
Asp Glu
```

<210> SEQ ID NO 29
<211> LENGTH: 208
<212> TYPE: PRT
<213> ORGANISM: Lethenteron camtschaticum
<220> FEATURE:
<221> NAME/KEY: misc_feature
<222> LOCATION: (1)..(208)
<223> OTHER INFORMATION: HMGB1

<400> SEQUENCE: 29

```
Met Gly Lys Gly Asp Pro Lys Pro Lys Gly Lys Met Ser Ser Tyr
1               5                   10                  15
Ala Tyr Phe Val Gln Thr Cys Arg Glu Glu His Lys Lys Lys Asn Pro
            20                  25                  30
Glu Ala Ser Val Asn Phe Ala Glu Phe Ser Lys Lys Cys Ser Glu Arg
        35                  40                  45
Trp Lys Thr Met Ser Glu Lys Glu Lys Thr Arg Phe Glu Asp Met Ala
    50                  55                  60
Lys Val Asp Lys Val Arg Tyr Asp Arg Glu Met Lys Thr Tyr Val Pro
65                  70                  75                  80
Pro Lys Gly Glu Arg Gly Ser Arg Lys Lys Asp Pro Asn Ala Pro
                85                  90                  95
Lys Arg Pro Pro Ser Ala Phe Phe Ile Tyr Cys Ala Glu Tyr Arg Ser
            100                 105                 110
Lys Val Arg Ala Glu Asn Pro Gly Leu Thr Ile Gly Ser Ile Ala Lys
        115                 120                 125
Lys Leu Gly Glu Met Trp Asn Asn Ala Pro Ala Asp Glu Lys Ser Ile
    130                 135                 140
Tyr Glu Arg Lys Thr Ala Lys Leu Lys Glu Lys Tyr Asp Lys Asp Met
145                 150                 155                 160
Ala Ser Tyr Arg Ser Lys Gly Lys Val Glu Thr Ser Lys Val Ala Ser
                165                 170                 175
```

```
Lys Pro Ala Ser Lys Gln Arg Asp Asp Asp Glu Asp Asp
            180                 185                 190

Glu Asp Glu Asp Glu Asp Glu Asp Asp Asp Asp Asp Glu
        195                 200                 205
```

<210> SEQ ID NO 30
<211> LENGTH: 172
<212> TYPE: PRT
<213> ORGANISM: Ctenopharyngodon idella
<220> FEATURE:
<221> NAME/KEY: misc_feature
<222> LOCATION: (1)..(172)
<223> OTHER INFORMATION: HMGB1

<400> SEQUENCE: 30

```
Met Gly Lys Asp Pro Arg Lys Pro Lys Gly Lys Met Ser Ser Tyr Ala
1               5                   10                  15

Tyr Phe Val Gln Thr Cys Arg Glu Glu His Lys Lys His Pro Glu
            20                  25                  30

Ala Thr Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Gln Asp Lys Val Arg Phe Glu Arg Glu Met Lys Asn Tyr Ile Pro Pro
65                  70                  75                  80

Lys Gly Glu Lys Lys Arg Arg Phe Lys Asp Pro Asn Ala Pro Lys Arg
                85                  90                  95

Pro Pro Ser Ala Phe Phe Ile Phe Cys Gly Asp Tyr Arg Pro Lys Ile
            100                 105                 110

Arg Gly Glu Asn Pro Gly Leu Ser Ile Gly Asp Ile Ala Lys Lys Leu
        115                 120                 125

Gly Glu Met Trp Asn Ser Ser Ala Glu Val Lys Gln Pro Tyr Glu
    130                 135                 140

Lys Lys Ala Ala Lys Leu Lys Glu Lys Tyr Asp Lys Asp Ile Ala Leu
145                 150                 155                 160

Tyr Arg Thr Lys Gly Ile Ala Gly Leu Ser Lys Lys
                165                 170
```

<210> SEQ ID NO 31
<211> LENGTH: 106
<212> TYPE: PRT
<213> ORGANISM: Ophiophagus hannah
<220> FEATURE:
<221> NAME/KEY: misc_feature
<222> LOCATION: (1)..(106)
<223> OTHER INFORMATION: HMGB1

<400> SEQUENCE: 31

```
Met Ala Lys Ala Asp Lys Val Arg Tyr Asp Arg Glu Met Lys Asp Tyr
1               5                   10                  15

Gly Pro Ala Lys Gly Gly Lys Lys Lys Asp Pro Asn Ala Pro Lys
            20                  25                  30

Arg Pro Pro Ser Gly Phe Phe Leu Phe Cys Ser Glu Phe Cys Ser Glu
        35                  40                  45

Phe Arg Pro Lys Ile Lys Ser Thr Asn Pro Gly Ile Ser Ile Gly Asp
    50                  55                  60

Val Ala Lys Lys Leu Gly Glu Met Trp Asn Asn Leu Ser Asp Ser Glu
65                  70                  75                  80

Lys Gly Pro Tyr Asn Asn Lys Ala Ala Lys Leu Lys Glu Lys Tyr Glu
```

```
                    85                  90                  95

Lys Val Arg Leu Gly Cys Trp Cys Trp Cys
                100                 105

<210> SEQ ID NO 32
<211> LENGTH: 51
<212> TYPE: PRT
<213> ORGANISM: Artemia franciscana
<220> FEATURE:
<221> NAME/KEY: misc_feature
<222> LOCATION: (1)..(51)
<223> OTHER INFORMATION: HMGB1

<400> SEQUENCE: 32

Met Pro Arg Ser Lys Asp Glu Ser Lys Pro Arg Gly Lys Leu Thr Ala
1               5                   10                  15

Tyr Ala Phe Phe Val Gln Thr Cys Arg Glu Glu His Lys Arg Lys His
                20                  25                  30

Pro Asp Glu Asn Val Val Phe Ala Glu Phe Ser Lys Lys Cys Ala Glu
            35                  40                  45

Arg Trp Lys
        50

<210> SEQ ID NO 33
<211> LENGTH: 85
<212> TYPE: PRT
<213> ORGANISM: Gallus gallus
<220> FEATURE:
<221> NAME/KEY: misc_feature
<222> LOCATION: (1)..(85)
<223> OTHER INFORMATION: HMGB1 box a1

<400> SEQUENCE: 33

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr
                85

<210> SEQ ID NO 34
<211> LENGTH: 54
<212> TYPE: PRT
<213> ORGANISM: Gallus gallus
<220> FEATURE:
<221> NAME/KEY: misc_feature
<222> LOCATION: (1)..(54)
<223> OTHER INFORMATION: HMGB1 box a2

<400> SEQUENCE: 34

Pro Asp Ala Ser Val Asn Phe Ser Glu Phe Ser Lys Lys Cys Ser Glu
1               5                   10                  15

Arg Trp Lys Thr Met Ser Ser Lys Glu Lys Gly Lys Phe Glu Asp Met
                20                  25                  30

Ala Lys Ala Asp Lys Leu Arg Tyr Glu Lys Glu Met Lys Asn Tyr Val
            35                  40                  45
```

Pro Pro Lys Gly Glu Thr
    50

<210> SEQ ID NO 35
<211> LENGTH: 73
<212> TYPE: PRT
<213> ORGANISM: Gallus gallus
<220> FEATURE:
<221> NAME/KEY: misc_feature
<222> LOCATION: (1)..(73)
<223> OTHER INFORMATION: HMGB1 box b1

<400> SEQUENCE: 35

Lys Asp Pro Asn Ala Pro Lys Arg Pro Pro Ser Ala Phe Phe Leu Phe
1               5                   10                  15

Cys Ser Glu Phe Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
        35                  40                  45

Ala Asp Asp Lys Gln Pro Tyr Glu Lys Lys Ala Ala Lys Leu Lys Glu
    50                  55                  60

Lys Tyr Glu Lys Asp Ile Ala Ala Tyr
65                  70

<210> SEQ ID NO 36
<211> LENGTH: 69
<212> TYPE: PRT
<213> ORGANISM: Gallus gallus
<220> FEATURE:
<221> NAME/KEY: misc_feature
<222> LOCATION: (1)..(69)
<223> OTHER INFORMATION: HMGB1 box b2

<400> SEQUENCE: 36

Asn Ala Pro Lys Arg Pro Pro Ser Ala Phe Phe Leu Phe Cys Ser Glu
1               5                   10                  15

Phe Arg Pro Lys Ile Lys Gly Glu His Pro Gly Leu Ser Ile Gly Asp
            20                  25                  30

Val Ala Lys Lys Leu Gly Glu Met Trp Asn Asn Thr Ala Ala Asp Asp
        35                  40                  45

Lys Gln Pro Tyr Glu Lys Lys Ala Ala Lys Leu Lys Glu Lys Tyr Glu
    50                  55                  60

Lys Asp Ile Ala Ala
65

<210> SEQ ID NO 37
<211> LENGTH: 21
<212> TYPE: PRT
<213> ORGANISM: Gallus gallus
<220> FEATURE:
<221> NAME/KEY: misc_feature
<222> LOCATION: (1)..(21)
<223> OTHER INFORMATION: HMGB1 RAGE binding domain

<400> SEQUENCE: 37

Lys Asp Pro Asn Ala Pro Lys Arg Pro Pro Ser Ala Phe Phe Leu Phe
1               5                   10                  15

Cys Ser Glu Phe Arg
            20

<210> SEQ ID NO 38
<211> LENGTH: 33

```
<212> TYPE: PRT
<213> ORGANISM: Gallus gallus
<220> FEATURE:
<221> NAME/KEY: misc_feature
<222> LOCATION: (1)..(33)
<223> OTHER INFORMATION: HMGB1 proinflammatory cytokine activity

<400> SEQUENCE: 38

Leu Lys Glu Lys Tyr Glu Lys Asp Ile Ala Ala Tyr Arg Ala Lys Gly
1               5                   10                  15

Lys Val Asp Ala Gly Lys Lys Val Val Ala Lys Ala Glu Lys Ser Lys
            20                  25                  30

Lys

<210> SEQ ID NO 39
<211> LENGTH: 182
<212> TYPE: PRT
<213> ORGANISM: Gallus gallus
<220> FEATURE:
<221> NAME/KEY: misc_feature
<222> LOCATION: (1)..(182)
<223> OTHER INFORMATION: Clostridium perfringens antigen

<400> SEQUENCE: 39

Ser Lys Glu Tyr Ala Arg Gly Phe Ala Lys Thr Gly Lys Ser Ile Tyr
1               5                   10                  15

Tyr Ser His Ala Ser Met Ser His Ser Trp Asp Asp Trp Asp Tyr Ala
            20                  25                  30

Ala Lys Val Thr Leu Ala Asn Ser Gln Lys Gly Thr Ala Gly Tyr Ile
        35                  40                  45

Tyr Arg Phe Leu His Asp Val Ser Glu Gly Asn Asp Pro Ser Val Gly
    50                  55                  60

Lys Asn Val Lys Glu Leu Val Ala Tyr Ile Ser Thr Ser Gly Glu Lys
65                  70                  75                  80

Asp Ala Gly Thr Asp Asp Tyr Met Tyr Phe Gly Ile Lys Thr Lys Asp
                85                  90                  95

Gly Lys Thr Gln Glu Trp Glu Met Asp Asn Pro Gly Asn Asp Phe Met
            100                 105                 110

Thr Gly Ser Lys Asp Thr Tyr Thr Phe Lys Leu Lys Asp Glu Asn Leu
        115                 120                 125

Lys Ile Asp Asp Ile Gln Asn Met Trp Ile Arg Lys Arg Lys Tyr Thr
    130                 135                 140

Ala Phe Pro Asp Ala Tyr Lys Pro Glu Asn Ile Lys Val Ile Ala Asn
145                 150                 155                 160

Gly Lys Val Val Val Asp Lys Asp Ile Asn Glu Trp Ile Ser Gly Asn
                165                 170                 175

Ser Thr Tyr Asn Ile Lys
            180

<210> SEQ ID NO 40
<211> LENGTH: 6
<212> TYPE: PRT
<213> ORGANISM: Clostridium perfringens
<220> FEATURE:
<221> NAME/KEY: misc_feature
<222> LOCATION: (1)..(6)
<223> OTHER INFORMATION: protective epitope of CPa

<400> SEQUENCE: 40

Ala Arg Gly Phe Ala Lys
1               5
```

-continued

```
<210> SEQ ID NO 41
<211> LENGTH: 8
<212> TYPE: PRT
<213> ORGANISM: Avian Influenza virus
<220> FEATURE:
<221> NAME/KEY: misc_feature
<222> LOCATION: (1)..(8)
<223> OTHER INFORMATION: Avian Influenza virus m2e

<400> SEQUENCE: 41

Glu Val Glu Thr Pro Ile Arg Asn
1               5

<210> SEQ ID NO 42
<211> LENGTH: 8
<212> TYPE: PRT
<213> ORGANISM: Avian Influenza virus
<220> FEATURE:
<221> NAME/KEY: misc_feature
<222> LOCATION: (1)..(8)
<223> OTHER INFORMATION: Avian Influenza virus m2e

<400> SEQUENCE: 42

Glu Val Glu Thr Pro Thr Arg Asn
1               5

<210> SEQ ID NO 43
<211> LENGTH: 12
<212> TYPE: PRT
<213> ORGANISM: Avian Influenza virus
<220> FEATURE:
<221> NAME/KEY: misc_feature
<222> LOCATION: (1)..(12)
<223> OTHER INFORMATION: Avian Influenza virus (HA5 UA)

<400> SEQUENCE: 43

Leu Leu Ser Arg Ile Asn His Phe Glu Lys Ile Gln
1               5                   10

<210> SEQ ID NO 44
<211> LENGTH: 19
<212> TYPE: PRT
<213> ORGANISM: Avian Influenza virus
<220> FEATURE:
<221> NAME/KEY: misc_feature
<222> LOCATION: (1)..(19)
<223> OTHER INFORMATION: Avian Influenza virus (HA5 LB)

<400> SEQUENCE: 44

Ala Asn Pro Ala Asn Asp Leu Cys Tyr Pro Gly Asp Phe Asn Asp Tyr
1               5                   10                  15

Glu Glu Leu

<210> SEQ ID NO 45
<211> LENGTH: 16
<212> TYPE: PRT
<213> ORGANISM: Avian Influenza virus
<220> FEATURE:
<221> NAME/KEY: misc_feature
<222> LOCATION: (1)..(16)
<223> OTHER INFORMATION: Avian Influenza virus (NP 54-69)

<400> SEQUENCE: 45

Gly Arg Leu Ile Gln Asn Ser Ile Thr Ile Glu Arg Met Val Leu Ser
1               5                   10                  15
```

-continued

<210> SEQ ID NO 46
<211> LENGTH: 14
<212> TYPE: PRT
<213> ORGANISM: Avian Influenza virus
<220> FEATURE:
<221> NAME/KEY: misc_feature
<222> LOCATION: (1)..(14)
<223> OTHER INFORMATION: Avian Influenza virus (NP 147-160)

<400> SEQUENCE: 46

```
Thr Tyr Gln Arg Thr Arg Ala Leu Val Arg Thr Gly Met Asp
1               5                   10
```

<210> SEQ ID NO 47
<211> LENGTH: 19
<212> TYPE: PRT
<213> ORGANISM: E. coli
<220> FEATURE:
<221> NAME/KEY: misc_feature
<222> LOCATION: (1)..(19)
<223> OTHER INFORMATION: PAL bis from E. coli

<400> SEQUENCE: 47

```
Glu Gly His Ala Asp Glu Arg Gly Thr Pro Glu Tyr Asn Ile Ser Leu
1               5                   10                  15

Gly Glu Arg
```

<210> SEQ ID NO 48
<211> LENGTH: 6
<212> TYPE: PRT
<213> ORGANISM: Artificial Sequence
<220> FEATURE:
<223> OTHER INFORMATION: Synthetic: peptide

<400> SEQUENCE: 48

```
Gly His Ala Asp Glu Arg
1               5
```

<210> SEQ ID NO 49
<211> LENGTH: 6
<212> TYPE: PRT
<213> ORGANISM: Artificial Sequence
<220> FEATURE:
<223> OTHER INFORMATION: Synthetic: peptide

<400> SEQUENCE: 49

```
Asp Glu Arg Gly Thr Pro
1               5
```

<210> SEQ ID NO 50
<211> LENGTH: 6
<212> TYPE: PRT
<213> ORGANISM: Artificial Sequence
<220> FEATURE:
<223> OTHER INFORMATION: Synthetic: peptide

<400> SEQUENCE: 50

```
Glu Tyr Asn Ile Ser Leu
1               5
```

<210> SEQ ID NO 51
<211> LENGTH: 6
<212> TYPE: PRT
<213> ORGANISM: Artificial Sequence
<220> FEATURE:
<223> OTHER INFORMATION: Synthetic: peptide

<400> SEQUENCE: 51

```
Ile Ser Leu Gly Glu Arg
1               5

<210> SEQ ID NO 52
<211> LENGTH: 19
<212> TYPE: PRT
<213> ORGANISM: Vibrio spp.
<220> FEATURE:
<221> NAME/KEY: misc_feature
<222> LOCATION: (1)..(19)
<223> OTHER INFORMATION: PALbis from vibrio spp.

<400> SEQUENCE: 52

Glu Gly His Ala Asp Glu Arg Gly Thr Pro Glu Tyr Asn Ile Ala Leu
1               5                   10                  15

Gly Glu Arg

<210> SEQ ID NO 53
<211> LENGTH: 17
<212> TYPE: PRT
<213> ORGANISM: Campylobacter spp.
<220> FEATURE:
<221> NAME/KEY: misc_feature
<222> LOCATION: (1)..(17)
<223> OTHER INFORMATION: corresponding peptide from Campylobacter spp.

<400> SEQUENCE: 53

Glu Gly Asn Cys Asp Glu Trp Gly Thr Asp Glu Tyr Asn Gln Ala Leu
1               5                   10                  15

Gly

<210> SEQ ID NO 54
<211> LENGTH: 19
<212> TYPE: PRT
<213> ORGANISM: E. coli
<220> FEATURE:
<221> NAME/KEY: misc_feature
<222> LOCATION: (1)..(19)
<223> OTHER INFORMATION: PAL from E. coli

<400> SEQUENCE: 54

Thr Val Glu Gly His Ala Asp Glu Arg Gly Thr Pro Glu Tyr Asn Ile
1               5                   10                  15

Ser Leu Gly

<210> SEQ ID NO 55
<211> LENGTH: 21
<212> TYPE: PRT
<213> ORGANISM: Campylobacter jejuni
<220> FEATURE:
<221> NAME/KEY: misc_feature
<222> LOCATION: (1)..(21)
<223> OTHER INFORMATION: Campylobacter jejuni Cj0113

<400> SEQUENCE: 55

Gly Val Ser Ile Thr Val Glu Gly Asn Cys Asp Glu Trp Gly Thr Asp
1               5                   10                  15

Glu Tyr Asn Gln Ala
            20

<210> SEQ ID NO 56
<211> LENGTH: 19
<212> TYPE: PRT
<213> ORGANISM: Vibrio spp.
<220> FEATURE:
```

<221> NAME/KEY: misc_feature
<222> LOCATION: (1)..(19)
<223> OTHER INFORMATION: Vibrio spp. alternative PAL epitope

<400> SEQUENCE: 56

Thr Val Glu Gly His Ala Asp Glu Arg Gly Thr Pro Glu Tyr Asn Ile
1 5 10 15

Ala Leu Gly

<210> SEQ ID NO 57
<211> LENGTH: 57
<212> TYPE: DNA
<213> ORGANISM: E. coli
<220> FEATURE:
<221> NAME/KEY: misc_feature
<222> LOCATION: (1)..(57)
<223> OTHER INFORMATION: E. coli nucleotide sequence for PAL epitope

<400> SEQUENCE: 57
gaaggtcacg cggacgaacg tggtaccccg gaatacaaca tctctctggg tgaacgt 57

<210> SEQ ID NO 58
<211> LENGTH: 9
<212> TYPE: PRT
<213> ORGANISM: E. coli
<220> FEATURE:
<221> NAME/KEY: misc_feature
<222> LOCATION: (1)..(9)
<223> OTHER INFORMATION: Epitope of PAL from E. coli

<400> SEQUENCE: 58

Glu Tyr Asn Ile Ser Leu Gly Glu Arg
1 5

<210> SEQ ID NO 59
<211> LENGTH: 9
<212> TYPE: PRT
<213> ORGANISM: Vibrio spp.
<220> FEATURE:
<221> NAME/KEY: misc_feature
<222> LOCATION: (1)..(9)
<223> OTHER INFORMATION: Epitope of PAL from Vibrio spp.

<400> SEQUENCE: 59

Glu Tyr Asn Ile Ala Leu Gly Glu Arg
1 5

<210> SEQ ID NO 60
<211> LENGTH: 16
<212> TYPE: PRT
<213> ORGANISM: Artificial Sequence
<220> FEATURE:
<223> OTHER INFORMATION: Synthetic: composite minimal epitope
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 60

Pro Xaa Xaa Xaa Xaa Xaa Gly Tyr Gly Ala Cys Glu Xaa Asn Leu Gly
1 5 10 15

<210> SEQ ID NO 61
<211> LENGTH: 43

-continued

```
<212> TYPE: PRT
<213> ORGANISM: Eimeria maxima
<220> FEATURE:
<221> NAME/KEY: misc_feature
<222> LOCATION: (1)..(43)
<223> OTHER INFORMATION: MPP; Eimeria maxima

<400> SEQUENCE: 61

Pro Ser His Asp Ala Pro Glu Ser Glu Arg Thr Pro Arg Val Ile Ser
1               5                   10                  15

Phe Gly Tyr Gly Ala Cys Glu His Asn Leu Gly Val Ser Leu Phe Arg
            20                  25                  30

Arg Glu Glu Thr Lys Lys Asp Pro Arg Gly Arg
        35                  40

<210> SEQ ID NO 62
<211> LENGTH: 28
<212> TYPE: PRT
<213> ORGANISM: Neospora canium
<220> FEATURE:
<221> NAME/KEY: misc_feature
<222> LOCATION: (1)..(28)
<223> OTHER INFORMATION: Neospora canium

<400> SEQUENCE: 62

Pro Arg Ile Val Ser Phe Gly Tyr Gly Ala Cys Glu His Asn Leu Gly
1               5                   10                  15

Met Ser Leu Tyr Asp Arg Gln Gly Leu Gln Arg Gln
            20                  25

<210> SEQ ID NO 63
<211> LENGTH: 21
<212> TYPE: PRT
<213> ORGANISM: Eimeria tenella
<220> FEATURE:
<221> NAME/KEY: misc_feature
<222> LOCATION: (1)..(21)
<223> OTHER INFORMATION: Eimeria tenella

<400> SEQUENCE: 63

Glu Ser Gln Arg Ala Pro Met Val Ile Arg Tyr Gly Tyr Gly Ala Cys
1               5                   10                  15

Glu Tyr Asn Leu Gly
            20

<210> SEQ ID NO 64
<211> LENGTH: 10
<212> TYPE: PRT
<213> ORGANISM: Eimeria maxima
<220> FEATURE:
<221> NAME/KEY: misc_feature
<222> LOCATION: (1)..(10)
<223> OTHER INFORMATION: Eimeria maxima TRAP-1

<400> SEQUENCE: 64

Gly Gly Gly Phe Pro Thr Ala Ala Val Ala
1               5                   10

<210> SEQ ID NO 65
<211> LENGTH: 40
<212> TYPE: PRT
<213> ORGANISM: Eimeria maxima
<220> FEATURE:
<221> NAME/KEY: misc_feature
<222> LOCATION: (1)..(40)
<223> OTHER INFORMATION: Eimeria maxima TRAP-02
```

```
<400> SEQUENCE: 65

Ala Ala Pro Glu Thr Pro Ala Val Gln Pro Lys Pro Glu Gly His
1               5                   10                  15

Glu Arg Pro Glu Pro Glu Glu Glu Lys Lys Glu Glu Gly Gly
            20                  25                  30

Gly Phe Pro Thr Ala Ala Val Ala
            35                  40

<210> SEQ ID NO 66
<211> LENGTH: 40
<212> TYPE: PRT
<213> ORGANISM: Eimeria maxima
<220> FEATURE:
<221> NAME/KEY: misc_feature
<222> LOCATION: (1)..(40)
<223> OTHER INFORMATION: Eimeria maxima TRAP-03

<400> SEQUENCE: 66

Gly Gly Gly Phe Pro Thr Ala Ala Val Ala Gly Gly Val Gly Val
1               5                   10                  15

Leu Leu Ile Ala Ala Val Gly Gly Val Ala Ala Phe Thr Ser Gly
            20                  25                  30

Gly Gly Gly Ala Gly Ala Gln Glu
            35                  40

<210> SEQ ID NO 67
<211> LENGTH: 21
<212> TYPE: PRT
<213> ORGANISM: Campylobacter jejuni
<220> FEATURE:
<221> NAME/KEY: misc_feature
<222> LOCATION: (1)..(21)
<223> OTHER INFORMATION: Campylobacter jejuni Cj0982

<400> SEQUENCE: 67

Lys Asp Ile Val Leu Asp Ala Glu Ile Gly Gly Val Ala Lys Gly Lys
1               5                   10                  15

Asp Gly Lys Glu Lys
            20

<210> SEQ ID NO 68
<211> LENGTH: 35
<212> TYPE: PRT
<213> ORGANISM: Campylobacter jejuni
<220> FEATURE:
<221> NAME/KEY: misc_feature
<222> LOCATION: (1)..(35)
<223> OTHER INFORMATION: Campylobacter jejuni Cj0420

<400> SEQUENCE: 68

Lys Val Ala Leu Gly Val Ala Val Pro Lys Asp Ser Asn Ile Thr Ser
1               5                   10                  15

Val Glu Asp Leu Lys Asp Lys Thr Leu Leu Leu Asn Lys Gly Thr Thr
            20                  25                  30

Ala Asp Ala
        35

<210> SEQ ID NO 69
<211> LENGTH: 16
<212> TYPE: PRT
<213> ORGANISM: Clostridium perfringens
<220> FEATURE:
<221> NAME/KEY: misc_feature
<222> LOCATION: (1)..(16)
```

<223> OTHER INFORMATION: Clostridium perfringens Alpha toxin

<400> SEQUENCE: 69

Asn Ala Trp Ser Lys Glu Tyr Ala Arg Gly Phe Ala Lys Thr Gly Lys
1               5                   10                  15

<210> SEQ ID NO 70
<211> LENGTH: 9
<212> TYPE: PRT
<213> ORGANISM: Avian influenza
<220> FEATURE:
<221> NAME/KEY: misc_feature
<222> LOCATION: (1)..(9)
<223> OTHER INFORMATION: Avian influenza M2e peptide

<400> SEQUENCE: 70

Cys Glu Val Glu Thr Pro Thr Arg Asn
1               5

<210> SEQ ID NO 71
<211> LENGTH: 9
<212> TYPE: PRT
<213> ORGANISM: Clostridium perfringens
<220> FEATURE:
<221> NAME/KEY: misc_feature
<222> LOCATION: (1)..(9)
<223> OTHER INFORMATION: 1-Alpha-31

<400> SEQUENCE: 71

Gly Lys Ile Asp Gly Thr Gly Thr His
1               5

<210> SEQ ID NO 72
<211> LENGTH: 15
<212> TYPE: PRT
<213> ORGANISM: Clostridium perfringens
<220> FEATURE:
<221> NAME/KEY: misc_feature
<222> LOCATION: (1)..(15)
<223> OTHER INFORMATION: 2-Alpha-51

<400> SEQUENCE: 72

Glu Asn Asp Met Ser Lys Asn Glu Pro Glu Ser Val Arg Lys Asn
1               5                   10                  15

<210> SEQ ID NO 73
<211> LENGTH: 20
<212> TYPE: PRT
<213> ORGANISM: Clostridium perfringens
<220> FEATURE:
<221> NAME/KEY: misc_feature
<222> LOCATION: (1)..(20)
<223> OTHER INFORMATION: 3-Alpha-71

<400> SEQUENCE: 73

Glu Asn Met His Glu Leu Gln Leu Gly Ser Thr Tyr Pro Asp Tyr Asp
1               5                   10                  15

Lys Asn Ala Tyr
            20

<210> SEQ ID NO 74
<211> LENGTH: 20
<212> TYPE: PRT
<213> ORGANISM: Clostridium perfringens
<220> FEATURE:
<221> NAME/KEY: misc_feature
<222> LOCATION: (1)..(20)
<223> OTHER INFORMATION: 4-Alpha-81

-continued

<400> SEQUENCE: 74

Thr Tyr Pro Asp Tyr Asp Lys Asn Ala Tyr Asp Leu Tyr Gln Asp His
1               5                   10                  15

Phe Trp Asp Pro
            20

<210> SEQ ID NO 75
<211> LENGTH: 20
<212> TYPE: PRT
<213> ORGANISM: Clostridium perfringens
<220> FEATURE:
<221> NAME/KEY: misc_feature
<222> LOCATION: (1)..(20)
<223> OTHER INFORMATION: 5-Alpha-91

<400> SEQUENCE: 75

Asp Leu Tyr Gln Asp His Phe Trp Asp Pro Asp Thr Asp Asn Asn Phe
1               5                   10                  15

Ser Lys Asp Asn
            20

<210> SEQ ID NO 76
<211> LENGTH: 10
<212> TYPE: PRT
<213> ORGANISM: Clostridium perfringens
<220> FEATURE:
<221> NAME/KEY: misc_feature
<222> LOCATION: (1)..(10)
<223> OTHER INFORMATION: 6-Alpha-117

<400> SEQUENCE: 76

Ile Pro Asp Thr Gly Glu Ser Gln Ile Arg
1               5                   10

<210> SEQ ID NO 77
<211> LENGTH: 10
<212> TYPE: PRT
<213> ORGANISM: Clostridium perfringens
<220> FEATURE:
<221> NAME/KEY: misc_feature
<222> LOCATION: (1)..(10)
<223> OTHER INFORMATION: 7-Alpha-136

<400> SEQUENCE: 77

Glu Trp Gln Arg Gly Asn Tyr Lys Gln Ala
1               5                   10

<210> SEQ ID NO 78
<211> LENGTH: 23
<212> TYPE: PRT
<213> ORGANISM: Clostridium perfringens
<220> FEATURE:
<221> NAME/KEY: misc_feature
<222> LOCATION: (1)..(23)
<223> OTHER INFORMATION: 8-Alpha-158

<400> SEQUENCE: 78

Asp Ile Asp Thr Pro Tyr His Pro Ala Asn Val Thr Ala Val Asp Ser
1               5                   10                  15

Ala Gly His Val Lys Phe Glu
            20

<210> SEQ ID NO 79
<211> LENGTH: 20
<212> TYPE: PRT

```
<213> ORGANISM: Clostridium perfringens
<220> FEATURE:
<221> NAME/KEY: misc_feature
<222> LOCATION: (1)..(20)
<223> OTHER INFORMATION: 9-Alpha-170

<400> SEQUENCE: 79

Val Asp Ser Ala Gly His Val Lys Phe Glu Thr Phe Ala Glu Glu Arg
1               5                   10                  15

Lys Glu Gln Tyr
            20

<210> SEQ ID NO 80
<211> LENGTH: 20
<212> TYPE: PRT
<213> ORGANISM: Clostridium perfringens
<220> FEATURE:
<221> NAME/KEY: misc_feature
<222> LOCATION: (1)..(20)
<223> OTHER INFORMATION: 10-Alpha-181

<400> SEQUENCE: 80

Thr Phe Ala Glu Glu Arg Lys Glu Gln Tyr Lys Ile Asn Thr Ala Gly
1               5                   10                  15

Cys Lys Thr Asn
            20

<210> SEQ ID NO 81
<211> LENGTH: 21
<212> TYPE: PRT
<213> ORGANISM: Clostridium perfringens
<220> FEATURE:
<221> NAME/KEY: misc_feature
<222> LOCATION: (1)..(21)
<223> OTHER INFORMATION: 11-Alpha-191

<400> SEQUENCE: 81

Lys Ile Asn Thr Val Gly Cys Lys Thr Asn Glu Asp Phe Tyr Ala Asp
1               5                   10                  15

Ile Leu Lys Asn Lys
            20

<210> SEQ ID NO 82
<211> LENGTH: 20
<212> TYPE: PRT
<213> ORGANISM: Clostridium perfringens
<220> FEATURE:
<221> NAME/KEY: misc_feature
<222> LOCATION: (1)..(20)
<223> OTHER INFORMATION: 12-Alpha-200

<400> SEQUENCE: 82

Glu Asp Phe Tyr Ala Asp Ile Leu Lys Asn Lys Asp Phe Asn Ala Trp
1               5                   10                  15

Ser Lys Glu Tyr
            20

<210> SEQ ID NO 83
<211> LENGTH: 20
<212> TYPE: PRT
<213> ORGANISM: Clostridium perfringens
<220> FEATURE:
<221> NAME/KEY: misc_feature
<222> LOCATION: (1)..(20)
<223> OTHER INFORMATION: 13-Alpha-210

<400> SEQUENCE: 83
```

Lys Asp Phe Asn Ala Trp Ser Lys Glu Tyr Ala Arg Gly Phe Ala Lys
1               5                   10                  15

Thr Gly Lys Ser
            20

<210> SEQ ID NO 84
<211> LENGTH: 17
<212> TYPE: PRT
<213> ORGANISM: Clostridium perfringens
<220> FEATURE:
<221> NAME/KEY: misc_feature
<222> LOCATION: (1)..(17)
<223> OTHER INFORMATION: 14-Alpha-220

<400> SEQUENCE: 84

Ala Arg Gly Phe Ala Lys Thr Gly Lys Ser Ile Tyr Tyr Ser His Ala
1               5                   10                  15

Ser

<210> SEQ ID NO 85
<211> LENGTH: 17
<212> TYPE: PRT
<213> ORGANISM: Clostridium perfringens
<220> FEATURE:
<221> NAME/KEY: misc_feature
<222> LOCATION: (1)..(17)
<223> OTHER INFORMATION: 15-Alpha-233

<400> SEQUENCE: 85

Ser His Ala Ser Met Ser His Ser Trp Asp Asp Trp Asp Tyr Ala Ala
1               5                   10                  15

Lys

<210> SEQ ID NO 86
<211> LENGTH: 20
<212> TYPE: PRT
<213> ORGANISM: Clostridium perfringens
<220> FEATURE:
<221> NAME/KEY: misc_feature
<222> LOCATION: (1)..(20)
<223> OTHER INFORMATION: 16-Alpha-240

<400> SEQUENCE: 86

Ser Trp Asp Asp Trp Asp Tyr Ala Ala Lys Val Thr Leu Ala Asn Ser
1               5                   10                  15

Gln Lys Gly Thr
            20

<210> SEQ ID NO 87
<211> LENGTH: 16
<212> TYPE: PRT
<213> ORGANISM: Clostridium perfringens
<220> FEATURE:
<221> NAME/KEY: misc_feature
<222> LOCATION: (1)..(16)
<223> OTHER INFORMATION: 17-Alpha-270

<400> SEQUENCE: 87

Asp Val Ser Glu Gly Asn Asp Pro Ser Val Gly Asn Asn Val Lys Glu
1               5                   10                  15

<210> SEQ ID NO 88
<211> LENGTH: 12
<212> TYPE: PRT
<213> ORGANISM: Clostridium perfringens

```
<220> FEATURE:
<221> NAME/KEY: misc_feature
<222> LOCATION: (1)..(12)
<223> OTHER INFORMATION: 18-Alpha-291

<400> SEQUENCE: 88

Ser Thr Ser Gly Glu Lys Asp Ala Gly Thr Asp Asp
1               5                   10

<210> SEQ ID NO 89
<211> LENGTH: 13
<212> TYPE: PRT
<213> ORGANISM: Clostridium perfringens
<220> FEATURE:
<221> NAME/KEY: misc_feature
<222> LOCATION: (1)..(13)
<223> OTHER INFORMATION: 19-Alpha-309

<400> SEQUENCE: 89

Lys Thr Lys Asp Gly Lys Thr Gln Glu Trp Glu Met Asp
1               5                   10

<210> SEQ ID NO 90
<211> LENGTH: 21
<212> TYPE: PRT
<213> ORGANISM: Clostridium perfringens
<220> FEATURE:
<221> NAME/KEY: misc_feature
<222> LOCATION: (1)..(21)
<223> OTHER INFORMATION: 20-Alpha-320

<400> SEQUENCE: 90

Asp Asn Pro Gly Asn Asp Phe Met Ala Gly Ser Lys Asp Thr Tyr Thr
1               5                   10                  15

Phe Lys Leu Lys Asp
                20

<210> SEQ ID NO 91
<211> LENGTH: 20
<212> TYPE: PRT
<213> ORGANISM: Clostridium perfringens
<220> FEATURE:
<221> NAME/KEY: misc_feature
<222> LOCATION: (1)..(20)
<223> OTHER INFORMATION: 21-Alpha-330

<400> SEQUENCE: 91

Ser Lys Asp Thr Tyr Thr Phe Lys Leu Lys Asp Glu Asn Leu Lys Ile
1               5                   10                  15

Asp Asp Ile Gln
                20

<210> SEQ ID NO 92
<211> LENGTH: 16
<212> TYPE: PRT
<213> ORGANISM: Clostridium perfringens
<220> FEATURE:
<221> NAME/KEY: misc_feature
<222> LOCATION: (1)..(16)
<223> OTHER INFORMATION: 22-Alpha-354

<400> SEQUENCE: 92

Arg Lys Arg Lys Tyr Thr Ala Phe Pro Asp Ala Tyr Lys Pro Glu Asn
1               5                   10                  15

<210> SEQ ID NO 93
<211> LENGTH: 19
```

```
<212> TYPE: PRT
<213> ORGANISM: Clostridium perfringens
<220> FEATURE:
<221> NAME/KEY: misc_feature
<222> LOCATION: (1

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Phe Arg Pro Lys
                100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Asp Glu Asp
                180                 185                 190

Glu Asp Glu Asp Glu Asp Glu Glu Glu Glu Glu Glu Asp
        195                 200                 205

Glu Asp Asp Asp Asp
        210
```

<210> SEQ ID NO 96
<211> LENGTH: 209
<212> TYPE: PRT
<213> ORGANISM: Tyto alba
<220> FEATURE:
<221> NAME/KEY: misc_feature
<222> LOCATION: (1)..(209)
<223> OTHER INFORMATION: High mobility group protein B1, partial

<400> SEQUENCE: 96

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Phe Arg Pro Lys
                100                 105                 110

Ile Lys Gly Glu His Pro Gly Leu Ser Ile Gly Asp Val Ala Lys Lys
        115                 120                 125
```

```
Leu Gly Glu Met Trp Asn Asn Thr Ala Ala Asp Asp Lys Gln Pro Tyr
    130                 135                 140
Glu Lys Lys Ala Ala Lys Leu Lys Glu Lys Tyr Glu Lys Asp Ile Ala
145                 150                 155                 160
Ala Tyr Arg Ala Lys Gly Lys Val Asp Ala Gly Lys Lys Val Val Ala
                165                 170                 175
Lys Ala Glu Lys Ser Lys Lys Lys Glu Glu Glu Asp Glu Asp
                180                 185                 190
Glu Asp Glu Glu Asp Glu Asp Glu Glu Glu Glu Glu Glu Asp
                195                 200                 205
Glu
```

<210> SEQ ID NO 97
<211> LENGTH: 209
<212> TYPE: PRT
<213> ORGANISM: Podiceps cristatus
<220> FEATURE:
<221> NAME/KEY: misc_feature
<222> LOCATION: (1)..(209)
<223> OTHER INFORMATION: High mobility group protein B1, partial

<400> SEQUENCE: 97

```
Met Gly Lys Gly Asp Pro Lys Lys Pro Arg Gly Lys Met Ser Ser Tyr
1               5                   10                  15
Ala Phe Phe Val Gln Thr Cys Arg Glu Glu His Lys Lys Lys His Pro
                20                  25                  30
Asp Ala Ser Val Asn Phe Ser Glu Phe Ser Lys Lys Cys Ser Glu Arg
                35                  40                  45
Trp Lys Thr Met Ser Ser Lys Glu Lys Gly Lys Phe Glu Asp Met Ala
50                  55                  60
Lys Ala Asp Lys Leu Arg Tyr Glu Lys Glu Met Lys Asn Tyr Val Pro
65                  70                  75                  80
Pro Lys Gly Glu Thr Lys Lys Lys Phe Lys Asp Pro Asn Ala Pro Lys
                85                  90                  95
Arg Pro Pro Ser Ala Phe Phe Leu Phe Cys Ser Glu Phe Arg Pro Lys
                100                 105                 110
Ile Lys Gly Glu His Pro Gly Leu Ser Ile Gly Asp Val Ala Lys Lys
                115                 120                 125
Leu Gly Glu Met Trp Asn Asn Thr Ala Ala Asp Asp Lys Gln Pro Tyr
    130                 135                 140
Glu Lys Lys Ala Ala Lys Leu Lys Glu Lys Tyr Glu Lys Asp Ile Ala
145                 150                 155                 160
Ala Tyr Arg Ala Lys Gly Lys Val Asp Ala Gly Lys Lys Val Val Ala
                165                 170                 175
Lys Ala Glu Lys Ser Lys Lys Lys Glu Glu Glu Asp Glu Asp
                180                 185                 190
Glu Asp Glu Glu Asp Glu Asp Glu Glu Glu Glu Glu Glu Asp Glu
                195                 200                 205
Asp
```

<210> SEQ ID NO 98
<211> LENGTH: 206
<212> TYPE: PRT
<213> ORGANISM: Chaetura pelagic
<220> FEATURE:
<221> NAME/KEY: misc_feature
<222> LOCATION: (1)..(206)
<223> OTHER INFORMATION: High mobility group protein B1, partial

<400> SEQUENCE: 98

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
        50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Phe Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
        130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Glu Asp Glu Asp
                180                 185                 190

Glu Asp Glu Glu Asp Glu Asp Glu Glu Glu Glu Glu Glu
            195                 200                 205
```

<210> SEQ ID NO 99
<211> LENGTH: 206
<212> TYPE: PRT
<213> ORGANISM: Tauraco erythrolphus
<220> FEATURE:
<221> NAME/KEY: misc_feature
<222> LOCATION: (1)..(206)
<223> OTHER INFORMATION: High mobility group protein B1, partial

<400> SEQUENCE: 99

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
        50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Phe Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
```

```
                130             135             140
Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Glu Asp Glu Asp
                180                 185                 190

Glu Glu Glu Glu Asp Glu Asp Asp Glu Glu Glu Glu Glu
        195                 200                 205
```

<210> SEQ ID NO 100
<211> LENGTH: 203
<212> TYPE: PRT
<213> ORGANISM: Phaethon lepturus
<220> FEATURE:
<221> NAME/KEY: misc_feature
<222> LOCATION: (1)..(203)
<223> OTHER INFORMATION: High mobility group protein B1, partial

<400> SEQUENCE: 100

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Phe Arg Pro Lys
            100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Glu Asp Glu Asp
                180                 185                 190

Glu Asp Glu Glu Asp Glu Asp Asp Glu Glu Glu
        195                 200
```

<210> SEQ ID NO 101
<211> LENGTH: 201
<212> TYPE: PRT
<213> ORGANISM: Pterocles gutturalis
<220> FEATURE:
<221> NAME/KEY: misc_feature
<222> LOCATION: (1)..(201)
<223> OTHER INFORMATION: High mobility group protein B1, partial

<400> SEQUENCE: 101

```
Met Gly Lys Gly Asp Pro Lys Lys Pro Arg Gly Lys Met Ser Ser Tyr
1               5                   10                  15
```

Ala Phe Phe Val Gln Thr Cys Arg Glu Glu His Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
 50                  55                  60

Lys Ala Asp Lys Leu Arg Tyr Glu Lys Glu Met Lys Asn Tyr Val Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Phe Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Thr Lys Lys Val Val Ala
                165                 170                 175

Lys Ala Glu Lys Ser Lys Lys Lys Glu Glu Glu Glu Asp Glu Asp
                180                 185                 190

Glu Asp Glu Glu Asp Glu Asp Asp Glu
                195                 200

<210> SEQ ID NO 102
<211> LENGTH: 200
<212> TYPE: PRT
<213> ORGANISM: Gavia stellata
<220> FEATURE:
<221> NAME/KEY: misc_feature
<222> LOCATION: (1)..(200)
<223> OTHER INFORMATION: High mobility group protein B1, partial

<400> SEQUENCE: 102

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
 50                  55                  60

Lys Ala Asp Lys Leu Arg Tyr Glu Lys Glu Met Lys Asn Tyr Val Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Phe Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

```
Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Glu Asp Glu Glu Asp
            180                 185                 190

Glu Asp Glu Glu Asp Glu Asp Glu
        195                 200

<210> SEQ ID NO 103
<211> LENGTH: 176
<212> TYPE: PRT
<213> ORGANISM: Nannospalax ehrenbergi
<220> FEATURE:
<221> NAME/KEY: misc_feature
<222> LOCATION: (1)..(176)
<223> OTHER INFORMATION: High mobility group protein

<400> SEQUENCE: 103

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Glu Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

<210> SEQ ID NO 104
<211> LENGTH: 176
<212> TYPE: PRT
<213> ORGANISM: Gekko japonicas
<220> FEATURE:
<221> NAME/KEY: misc_feature
<222> LOCATION: (1)..(176)
<223> OTHER INFORMATION: High mobility group protein B1

<400> SEQUENCE: 104

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
```

```
                65                  70                  75                  80
Pro Lys Gly Glu Thr Lys Lys Phe Glu Asp Pro Asn Ala Pro Lys
                    85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

<210> SEQ ID NO 105
<211> LENGTH: 175
<212> TYPE: PRT
<213> ORGANISM: Tupaia chinensis
<220> FEATURE:
<221> NAME/KEY: misc_feature
<222> LOCATION: (1)..(175)
<223> OTHER INFORMATION: High mobility group protein B1

<400> SEQUENCE: 105

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala His Tyr Glu Arg Glu Met Lys Thr Phe Ile Pro
65                  70                  75                  80

Pro Lys Gly Glu Thr Lys Lys Phe Lys Asp Pro Asn Ala Pro Lys
                    85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ser Lys Lys Gly Val
                165                 170                 175

<210> SEQ ID NO 106
<211> LENGTH: 272
<212> TYPE: PRT
<213> ORGANISM: Gallus gallus
<220> FEATURE:
<221> NAME/KEY: misc_feature
<222> LOCATION: (1)..(272)
<223> OTHER INFORMATION: CD154 chicken (Gallus gallus)

<400> SEQUENCE: 106

Met Asn Glu Ala Tyr Ser Pro Ala Ala Pro Arg Pro Met Gly Ser Thr
1               5                   10                  15
```

```
Ser Pro Ser Thr Met Lys Met Phe Met Cys Phe Leu Ser Val Phe Met
            20                  25                  30

Val Val Gln Thr Ile Gly Thr Val Leu Phe Cys Leu Tyr Leu His Met
        35                  40                  45

Lys Met Asp Lys Met Glu Glu Val Leu Ser Leu Asn Glu Asp Tyr Ile
    50                  55                  60

Phe Leu Arg Lys Val Gln Lys Cys Gln Thr Gly Glu Asp Gln Lys Ser
65                  70                  75                  80

Thr Leu Leu Asp Cys Glu Lys Val Leu Lys Gly Phe Gln Asp Leu Gln
                85                  90                  95

Cys Lys Asp Arg Thr Ala Ser Glu Glu Leu Pro Lys Phe Glu Met His
            100                 105                 110

Arg Gly His Glu His Pro His Leu Lys Ser Arg Asn Glu Thr Ser Val
        115                 120                 125

Ala Glu Glu Lys Arg Gln Pro Ile Ala Thr His Leu Ala Gly Val Lys
    130                 135                 140

Ser Asn Thr Thr Val Arg Val Leu Lys Trp Met Thr Thr Ser Tyr Ala
145                 150                 155                 160

Pro Thr Ser Ser Leu Ile Ser Tyr His Glu Gly Lys Leu Lys Val Glu
                165                 170                 175

Lys Ala Gly Leu Tyr Tyr Ile Tyr Ser Gln Val Ser Phe Cys Thr Lys
            180                 185                 190

Ala Ala Ala Ser Ala Pro Phe Thr Leu Tyr Ile Tyr Leu Tyr Leu Pro
        195                 200                 205

Met Glu Glu Asp Arg Leu Leu Met Lys Gly Leu Asp Thr His Ser Thr
    210                 215                 220

Ser Thr Ala Leu Cys Glu Leu Gln Ser Ile Arg Glu Gly Gly Val Phe
225                 230                 235                 240

Glu Leu Arg Gln Gly Asp Met Val Phe Val Asn Val Thr Asp Ser Thr
                245                 250                 255

Ala Val Asn Val Asn Pro Gly Asn Thr Tyr Phe Gly Met Phe Lys Leu
            260                 265                 270

<210> SEQ ID NO 107
<211> LENGTH: 261
<212> TYPE: PRT
<213> ORGANISM: Homo sapiens
<220> FEATURE:
<221> NAME/KEY: misc_feature
<222> LOCATION: (1)..(261)
<223> OTHER INFORMATION: CD154 human Homo sapiens

<400> SEQUENCE: 107

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95
```

```
Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 108
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: CD154 partial human Homo sapiens

<400> SEQUENCE: 108

Trp Ala Glu Lys Gly Tyr Tyr Thr Met Ser Cys
1               5                   10

<210> SEQ ID NO 109
<211> LENGTH: 11
<212> TYPE: PRT
<213> ORGANISM: Gallus gallus
<220> FEATURE:
<221> NAME/KEY: misc_feature
<222> LOCATION: (1)..(11)
<223> OTHER INFORMATION: Chicken CD154 peptide Gallus gallus

<400> SEQUENCE: 109

Trp Met Thr Thr Ser Tyr Ala Pro Thr Ser Ser
1               5                   10

<210> SEQ ID NO 110
<211> LENGTH: 10
<212> TYPE: PRT
<213> ORGANISM: Anas sp.
<220> FEATURE:
<221> NAME/KEY: misc_feature
<222> LOCATION: (1)..(10)
<223> OTHER INFORMATION: Duck CD154 peptide (Anas sp.)

<400> SEQUENCE: 110

Trp Asn Lys Thr Ser Tyr Ala Pro Met Asn
1               5                   10
```

-continued

```
<210> SEQ ID NO 111
<211> LENGTH: 10
<212> TYPE: PRT
<213> ORGANISM: Mus sp.
<220> FEATURE:
<221> NAME/KEY: misc_feature
<222> LOCATION: (1)..(10)
<223> OTHER INFORMATION: Mouse CD154 peptide (Mus p.)

<400> SEQUENCE: 111

Trp Ala Lys Lys Gly Tyr Tyr Thr Met Lys
1               5                   10

<210> SEQ ID NO 112
<211> LENGTH: 10
<212> TYPE: PRT
<213> ORGANISM: Bos taurus
<220> FEATURE:
<221> NAME/KEY: misc_feature
<222> LOCATION: (1)..(10)
<223> OTHER INFORMATION: Cow CD154 peptide (Bos taurus)

<400> SEQUENCE: 112

Trp Ala Pro Lys Gly Tyr Tyr Thr Leu Ser
1               5                   10

<210> SEQ ID NO 113
<211> LENGTH: 139
<212> TYPE: PRT
<213> ORGANISM: Artificial Sequence
<220> FEATURE:
<223> OTHER INFORMATION: Synthetic: Heavy chain, Leader
      sequence-FR1-CDR1-FR2-CDR2-FR3-CDR3-FR4

<400> SEQUENCE: 113

Met Ala Val Leu Ala Leu Leu Cys Leu Val Ala Phe Pro Ser Cys
1               5                   10                  15

Thr Leu Ser Gln Val Gln Leu Lys Glu Ser Gly Pro Gly Leu Val Ala
                20                  25                  30

Pro Ser Gln Ser Leu Ser Ile Thr Cys Thr Val Ser Gly Phe Ser Leu
            35                  40                  45

Thr Thr Tyr Asp Ile Asn Trp Ile Arg Gln Pro Pro Gly Lys Gly Leu
    50                  55                  60

Glu Trp Leu Gly Ile Ile Trp Thr Gly Gly Thr Asn Tyr Asn Ser
65                  70                  75                  80

Ala Phe Met Ser Arg Leu Ser Ile Ser Lys Asp Asn Ser Lys Ser Gln
                85                  90                  95

Val Phe Leu Lys Met Asn Ser Leu Gln Thr Asp Asp Thr Ala Ile Tyr
            100                 105                 110

Tyr Cys Val Arg Asp Arg Gly Tyr Tyr Val Tyr Tyr Ser Met Asp Tyr
        115                 120                 125

Trp Gly Gln Gly Thr Ser Val Thr Val Ser Ser
    130                 135

<210> SEQ ID NO 114
<211> LENGTH: 127
<212> TYPE: PRT
<213> ORGANISM: Artificial Sequence
<220> FEATURE:
<223> OTHER INFORMATION: Synthetic: Light chain, Leader
      sequence-FR1-CDR1-FR2-CDR2-FR3-CDR3-FR4

<400> SEQUENCE: 114

Met Met Ser Ser Ala Gln Phe Leu Gly Leu Leu Leu Leu Cys Phe Gln
```

```
1               5                   10                  15
Gly Thr Arg Cys Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
                35                  40                  45

Ile Ser Asn Tyr Leu Asn Trp Tyr Gln Gln Lys Pro Asp Gly Thr Val
50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
                100                 105                 110

Met Phe Pro Trp Thr Phe Gly Gly Gly Thr Lys Leu Glu Ile Lys
                115                 120                 125

<210> SEQ ID NO 115
<211> LENGTH: 264
<212> TYPE: PRT
<213> ORGANISM: Artificial Sequence
<220> FEATURE:
<223> OTHER INFORMATION: Synthetic: amino acid

<400> SEQUENCE: 115

Met Thr Gln Ser Gln Lys Phe Met Ser Thr Ser Val Gly Asp Arg Val
1               5                   10                  15

Ser Val Thr Cys Lys Ala Ser Gln Asn Val Gly Thr Asn Val Ala Trp
                20                  25                  30

Tyr Gln Gln Lys Pro Gly Gln Ser Pro Lys Ala Leu Ile Tyr Ser Ala
                35                  40                  45

Ser Tyr Arg Tyr Ser Gly Val Pro Asp Arg Phe Thr Gly Ser Gly Ser
                50                  55                  60

Gly Thr Asp Phe Thr Leu Thr Ile Ser Asn Val Gln Ser Glu Asp Leu
65                  70                  75                  80

Ala Asp Tyr Phe Cys Gln Gln Tyr Ser Ser Tyr Pro Leu Thr Phe Gly
                85                  90                  95

Gly Gly Thr Lys Leu Glu Ile Lys Gly Gly Ser Ser Arg Ser Ser Leu
                100                 105                 110

Glu Val Gln Leu Gln Gln Ser Gly Ala Glu Leu Val Lys Pro Gly Thr
                115                 120                 125

Ser Val Arg Ile Ser Cys Lys Ala Ser Gly Tyr Thr Phe Thr Asn Tyr
                130                 135                 140

Tyr Ile Tyr Trp Val Lys Gln Arg Pro Gly Gln Gly Leu Glu Trp Ile
145                 150                 155                 160

Gly Trp Ile Tyr Pro Gly Asn Val Asn Thr Lys Tyr Asn Glu Lys Phe
                165                 170                 175

Lys Gly Lys Ala Thr Leu Thr Val Asp Lys Ser Ser Ser Thr Ala Tyr
                180                 185                 190

Met Gln Leu Ser Ser Leu Thr Ser Glu Asp Ser Ala Val Tyr Phe Cys
                195                 200                 205

Ala Arg Arg Gly Thr Gly Thr Val Val Phe Asp Tyr Trp Gly His Gly
                210                 215                 220

Thr Thr Leu Thr Val Ser Ser Ala Lys Thr Thr Pro Pro Ser Val Thr
225                 230                 235                 240

Ser Gly Gln Ala Gly Gln His His His His His His Gly Ala Tyr Pro
```

Tyr Asp Val Pro Asp Tyr Ala Ser
        260

<210> SEQ ID NO 116
<211> LENGTH: 10
<212> TYPE: PRT
<213> ORGANISM: Artificial Sequence
<220> FEATURE:
<223> OTHER INFORMATION: Synthetic: Heavy chain CDR1

<400> SEQUENCE: 116

Gly Phe Ser Leu Thr Thr Tyr Asp Ile Asn
1               5                   10

<210> SEQ ID NO 117
<211> LENGTH: 16
<212> TYPE: PRT
<213> ORGANISM: Artificial Sequence
<220> FEATURE:
<223> OTHER INFORMATION: Synthetic: Heavy chain CDR2

<400> SEQUENCE: 117

Ile Ile Trp Thr Gly Gly Gly Thr Asn Tyr Asn Ser Ala Phe Met Ser
1               5                   10                  15

<210> SEQ ID NO 118
<211> LENGTH: 12
<212> TYPE: PRT
<213> ORGANISM: Artificial Sequence
<220> FEATURE:
<223> OTHER INFORMATION: Synthetic: Heavy chain CDR3

<400> SEQUENCE: 118

Asp Arg Gly Tyr Tyr Val Tyr Tyr Ser Met Asp Tyr
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic: Light chain CDR1

<400> SEQUENCE: 119

Arg Ala Ser Gln Asp Ile Ser Asn Tyr Leu Asn
1               5                   10

<210> SEQ ID NO 120
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 120

Tyr Thr Ser Arg Leu His Ser
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic: Light chain CDR3

<400> SEQUENCE: 121

```
Gln Gln Gly Asn Met Phe Pro Trp Thr
1               5
```

<210> SEQ ID NO 122
<211> LENGTH: 5
<212> TYPE: PRT
<213> ORGANISM: Artificial Sequence
<220> FEATURE:
<223> OTHER INFORMATION: Synthetic: VH, CDR1

<400> SEQUENCE: 122

```
Asn Tyr Tyr Ile Tyr
1               5
```

<210> SEQ ID NO 123
<211> LENGTH: 17
<212> TYPE: PRT
<213> ORGANISM: Artificial Sequence
<220> FEATURE:
<223> OTHER INFORMATION: Synthetic: VH, CDR2

<400> SEQUENCE: 123

```
Trp Ile Tyr Pro Gly Asn Val Asn Thr Lys Tyr Asn Glu Lys Phe Lys
1               5                   10                  15

Gly
```

<210> SEQ ID NO 124
<211> LENGTH: 11
<212> TYPE: PRT
<213> ORGANISM: Artificial Sequence
<220> FEATURE:
<223> OTHER INFORMATION: Synthetic: VH, CDR3

<400> SEQUENCE: 124

```
Arg Gly Thr Gly Thr Val Val Phe Asp Tyr Trp
1               5                   10
```

<210> SEQ ID NO 125
<211> LENGTH: 11
<212> TYPE: PRT
<213> ORGANISM: Artificial Sequence
<220> FEATURE:
<223> OTHER INFORMATION: Synthetic: VL, CDR1

<400> SEQUENCE: 125

```
Lys Ala Ser Gln Asn Val Gly Thr Asn Val Ala
1               5                   10
```

<210> SEQ ID NO 126
<211> LENGTH: 7
<212> TYPE: PRT
<213> ORGANISM: Artificial Sequence
<220> FEATURE:
<223> OTHER INFORMATION: Synthetic: VL, CDR2

<400> SEQUENCE: 126

```
Ser Ala Ser Tyr Arg Tyr Ser
1               5
```

<210> SEQ ID NO 127
<211> LENGTH: 9
<212> TYPE: PRT
<213> ORGANISM: Artificial Sequence
<220> FEATURE:
<223> OTHER INFORMATION: Synthetic: VL, CDR3

```
<400> SEQUENCE: 127

Gln Gln Tyr Ser Ser Tyr Pro Leu Thr
1               5

<210> SEQ ID NO 128
<211> LENGTH: 21
<212> TYPE: DNA
<213> ORGANISM: Artificial Sequence
<220> FEATURE:
<223> OTHER INFORMATION: Synthetic: AOXSeqF

<400> SEQUENCE: 128
gactggttcc aattgacaag c                                              21

<210> SEQ ID NO 129
<211> LENGTH: 21
<212> TYPE: DNA
<213> ORGANISM: Artificial Sequence
<220> FEATURE:
<223> OTHER INFORMATION: Synthetic: AOXSeqR

<400> SEQUENCE: 129
gcaaatggca ttctgacatc c                                              21
```

YEAST VACCINE VECTOR INCLUDING IMMUNOSTIMULATORY AND ANTIGENIC POLYPEPTIDES AND METHODS OF USING THE SAME

CROSS-REFERENCE TO RELATED PATENT APPLICATIONS

The present application claims the benefit of priority to U.S. Provisional Patent Application No. 62/331,044, filed on May 3, 2016, the contents of which are incorporated herein by reference in its entirety.

SEQUENCE LISTING

This application is being filed electronically via EFS-Web and includes an electronically submitted Sequence Listing in .txt format. The .txt file contains a sequence listing entitled "2017-05-01_5658-00380_ST25.txt" created on May 2, 2017 and is 118,371 bytes in size. The Sequence Listing contained in this .txt file is part of the specification and is hereby incorporated by reference herein in its entirety.

INTRODUCTION

Vaccines are used to initiate an adaptive immune response against antigens, in particular antigens from pathogens in order to ameliorate or prevent disease. Inactivated or attenuated microorganism vaccines are often effective at stimulating a robust immune response that is fully protective, but in some cases these vaccines are not protective or only partially protective and other strategies must be used to develop protective vaccines. Microorganism based vaccines cannot post-translationally modify proteins by glycosylation to properly express large antigenic proteins, such as viral proteins; therefore, development of a yeast vaccine vector that can glycosylate and result in properly folded large antigenic proteins that is safe and effective at stimulating a lasting protective immune response is needed.

SUMMARY

Yeast vaccine vectors are provided herein. The vaccine vectors are suitable for oral administration and produce rapid and long-lasting immunity to the antigens and protection from subsequent infection with the targeted microorganism. In particular the immune response generated is an IgA response suitable for protection from mucosal infections.

In one aspect, a yeast vaccine composition is provided. The composition includes a yeast comprising an immunostimulatory polynucleotide encoding an immunostimulatory polypeptide selected from an HMGB1 polypeptide or a CD40 ligand. The yeast is engineered to express the HMGB1 polypeptide or the CD40 ligand on the surface of the yeast. The compositions may also include an antigenic polypeptide, suitably expressed on the surface of the yeast as well. The compositions may be combined with pharmaceutically acceptable carriers and/or adjuvants to generate pharmaceutical compositions. The compositions may include more than one antigenic polypeptide and the more than one antigenic polypeptides may be derived from the same or different organism or species.

In another aspect, methods of enhancing an immune response in a subject by administering the vaccine compositions and pharmaceutical compositions provided herein to the subject in an amount effective to enhance the immune response of the subject to the vaccine composition and the infectious agent related to the antigenic polypeptides.

BRIEF DESCRIPTION OF THE DRAWINGS

FIGS. 3A-3F are a set of photographs showing HMGB1 cell surface expression on *Pichia pastoris* (X33). *Pichia pastoris*-HMGB1 construct #4 (FIG. 3D: DIC only, FIG. 3E: fluorescence only, FIG. 3F: DIC/fluorescence overlay) and *Pichia pastoris* (X33; FIG. 3A: DIC only, FIG. 3B: fluorescence only, FIG. 3C: DIC/fluorescence overlay) backbone were stained using rabbit polyclonal HMGB1 156-177 diluted 1:5 in phosphate buffered saline (PBS) with the $F(ab)^2$ portion of goat anti-rabbit IgG conjugated with ALEXA 488® at 1:1000 in 1% goat serum in PBS. HMGB1 protein expression was optimally expressed on three of the nine *Pichia pastoris*-HMGB1 constructs that were transformed.

FIG. 7 is a graph showing the distribution of all lesion scores was also decreased in the vaccinated animals. The vaccinated animals demonstrated lower lesion scores.

DETAILED DESCRIPTION

Figure 1:
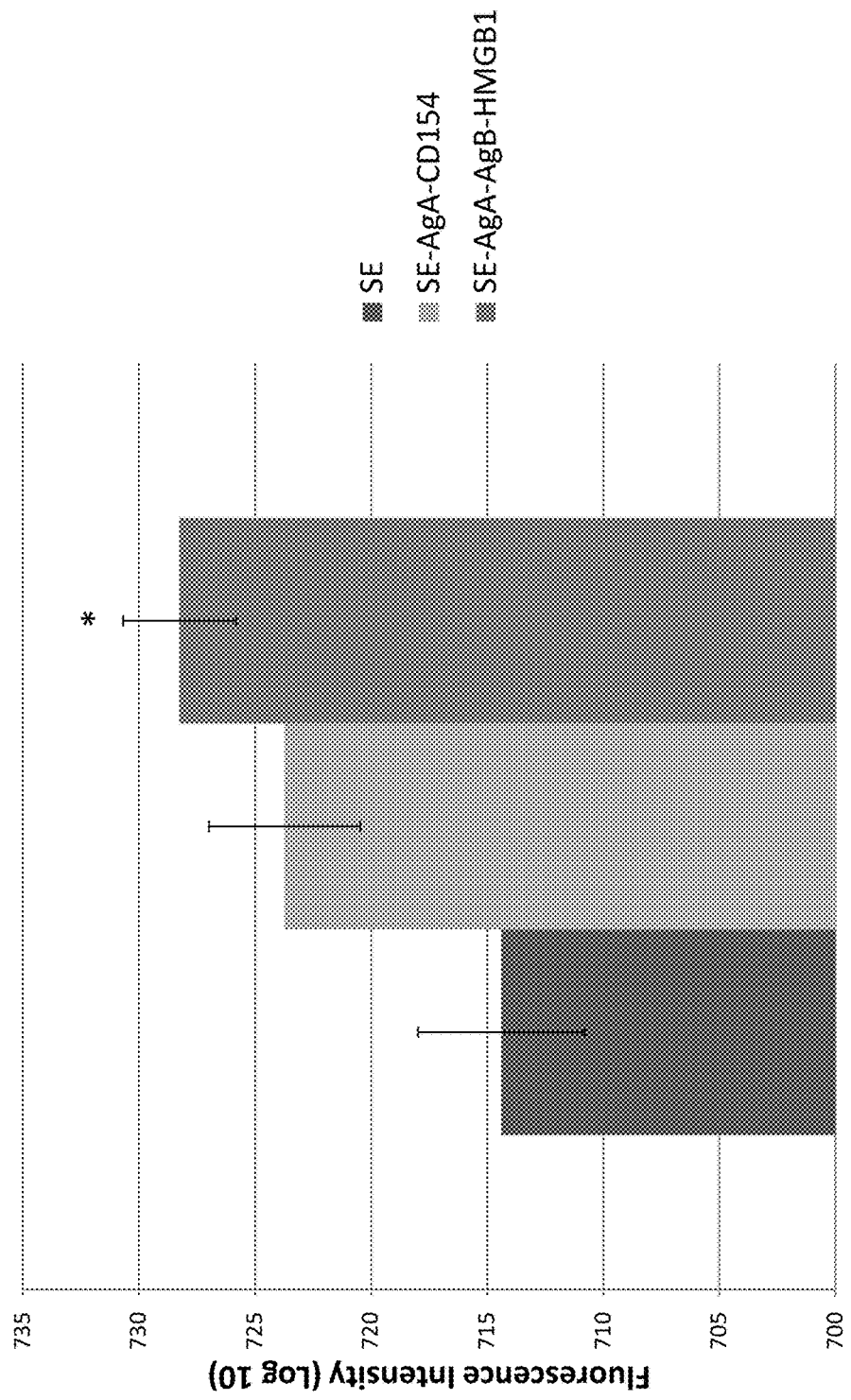
FIG. 1 is a graph comparing the fluorescence intensity of RAW 264 macrophages after co-culture with fluorescent labeled with *Salmonella Enteriditis* aroA/htrA, *Salmonella Enteriditis* aroA/htrA-AgA-CD154, and *Salmonella Enteriditis* aroA/htrA-AgA-AgB-HMGB1.

A vaccine composition capable of eliciting an immune response against the vaccine composition or against an antigenic polypeptide expressed by the vaccine composition is provided herein. In particular the vaccine composition includes a yeast engineered to express an immunostimulatory polypeptide on its surface. The yeast may also be engineered to express additional antigenic polypeptides on the surface of the yeast. In particular embodiments, a *Pichia pastoris* vaccine vector is provided. The vaccine vector includes an immunostimulatory polynucleotide sequence encoding an immunostimulatory polypeptide which is displayed or expressed on the surface of the yeast. The immunostimulatory polypeptide may be a high mobility group box 1 (HMGB1) immunostimulatory polypeptide or a CD40 ligand such as CD154 polypeptide or a fragment thereof or other CD40 agonist such as a CD40 agonistic antibody. The immunostimulatory polypeptide may be expressed on the surface of the yeast, e.g., *Pichia pastoris*, using any means available to those of skill in the art. In the examples the immunostimulatory polypeptide is attached to the surface of the yeast via a glycosylphosphatidylinositol (GPI)-anchored mechanism encoded by the 3' end of *Saccharomyces cerevisiae* α-agglutinin. Those skilled in the art will readily appreciate that other expression systems may be used to obtain surface expression of the immunostimulatory and/or antigenic polypeptides included in the yeast to generate the vaccine compositions.

The HMGB1 protein was first identified as a DNA-binding protein critical for DNA structure and stability. It is a ubiquitously expressed nuclear protein that binds DNA with no sequence specificity. The protein is highly conserved and found in organisms ranging from plants to mammals. The chicken, zebrafish, human, mouse, rat, crab-eating *macaca*, cow, horse, canine, pig, rabbit, red drum, catfish, humphead snapper, goldfish, king cobra, brine shrimp and other HMGB1 amino acid sequences are provided. See SEQ ID NOs: 2-30 and 94-105. The sequence throughout mammals is highly conserved with 95% amino acid identity and the amino acid changes are conservative. Thus an HMGB1 protein from one species may likely substitute for that from another species functionally. The full-length HMGB1 protein or a portion thereof may be used as the HMGB1 polypeptide in the vaccine vectors described herein. HMGB1 has two DNA binding regions termed A1 and A2 and B1 and B2. See Andersson and Tracey, Annu. Rev. Immunol. 2011, 29:139-162.

HMGB1 is a mediator of inflammation and serves as a signal of nuclear damage, such as from necrotic cells. HMGB1 can also be actively secreted by cells of the monocyte/macrophage lineage in a process requiring acetylation of the protein, translocation across the nucleus, and secretion. Extracellular HMGB1 acts as a potent mediator of inflammation by signaling via the Receptor for Advanced Glycated End-products (RAGE) and via members of the Toll-like Receptor family (TLR), in particular TLR4. The RAGE binding activity has been identified and requires the polypeptide of the HMGB1 RAGE binding domain. TLR4 binding requires the cysteine at position 106 of the chicken HMGB1 sequence (SEQ ID NO: 2), which is found in the B box region of HMGB1.

Suitably, the vaccine vector contains a polynucleotide encoding a polypeptide including amino acids 150-183 and 89-109 of the chicken HMGB1 polypeptide or a homolog thereof. See SEQ ID NO: 2. In the Examples, a 190 amino acid polypeptide of HMGB1 was used. Suitably, the polynucleotide encodes a HMGB1 polypeptide from the same species as the subject in which the vaccine composition will be used. Heterologous combinations of HMGB1 polypeptides and subjects (i.e. a human HMGB1 polypeptide for use in a chicken vaccine) may be useful in the methods of the invention because HMGB1 is highly conserved through a wide number of species as discussed above. The HMGB1 polypeptide may be used to enhance the immune response in the subject to any foreign antigen or antigenic polypeptide present in or on the yeast vaccine compositions. One of skill in the art will appreciate that the HMGB1 polypeptide could be used to enhance the immune response to more than one antigenic polypeptide present in a yeast vaccine composition. The polypeptide from HMGB1 stimulates an immune response at least in part by activating dendritic cells and macrophages and thus stimulating production of cytokines such as IL-1, IL-6, IFN-γ and TNF-α. In the Examples, a polypeptide of HMGB1 was expressed on the surface of the vaccine compositions.

The inflammatory activities of HMGB1 do not require the full-length protein and functional fragments have been identified. The B box has been shown to be sufficient to mediate the pro-inflammatory effects of HMGB1 and thus HMGB1 box b1 and HMGB1 box b2 are HMGB1 polypeptides or functional fragments thereof within the context of the present invention. See e.g. SEQ ID NO: 35 and 36. In addition, the RAGE binding site and the pro-inflammatory cytokine activity have been mapped. See SEQ ID NO: 37 and 38, respectively. Thus, these polypeptides are functional fragments of HMGB1 polypeptides in the context of the present invention. See SEQ ID NOs: 31-38.

Those of skill in the art are capable of identifying HMGB1 polypeptides and fragments thereof capable of stimulating pro-inflammatory cytokine activity, using methods such as those in International Publication No. WO2002 092004, which is incorporated herein by reference in its entirety. Suitably, the HMGB1 polypeptide includes the RAGE binding domain at amino acids 150-183 of the chicken HMGB1 sequence (HMGB1 RAGE binding domain or a homolog thereof) and the pro-inflammatory cytokine activity domain between amino acids 89-109 of the chicken HMGB1 sequence (SEQ ID NO: 2; HMGB1 proinflammatory cytokine activity or a homolog thereof). In particular, HMGB1 polypeptides and functional fragments or homologs thereof include polypeptides identical to, or at least 99% identical, at least 98% identical, at least 95% identical, at least 90% identical, at least 85% identical, or at least 80% identical to the HMGB1 polypeptides of the chicken HMGB1 sequence or HMGB1 box a1, HMGB1 box a2, HMGB1 box b1, HMGB1 box b2, HMGB1 RAGE binding domain, or HMGB1 proinflammatory cytokine activity, respectively.

The immunostimulatory polypeptide may also be a CD40 ligand or CD40 agonist. A CD154 polypeptide that is capable of binding CD40 in the subject and stimulating the subject to respond to the vaccine composition and its associated foreign antigenic polypeptide may be used as the immunostimulatory polypeptide. The CD154 polypeptide may be full-length CD154 or may be fewer than 50 amino acids long, more suitably fewer than 40, fewer than 30 or fewer than 20 amino acids in length. The polypeptide may be between 10 and 15 amino acids, between 10 and 20 amino acids or between 10 and 25 amino acids in length. The CD154 sequence and CD40 binding region are not highly conserved among various species. The CD154 sequences of chicken and human are provided in SEQ ID NO: 106 and SEQ ID NO: 107, respectively.

The CD40 binding regions of CD154 have been determined for a number of species, including human, chicken, duck, mouse and cattle and are shown in SEQ ID NO: 108, SEQ ID NO: 109, SEQ ID NO: 110, SEQ ID NO:111, and SEQ ID NO:112, respectively. Also included are polypeptides identical to, or at least 99% identical, at least 98% identical, at least 95% identical, at least 90% identical, at least 85% identical, or at least 80% identical to the CD154 sequences provided in SEQ ID NOs: 106-112. Although there is variability in the sequences in the CD40 binding region between species, cross-species binding of CD154 to CD40 has been reported. For example, the human CD154 polypeptide was able to enhance the immune response in chickens. Therefore, one may practice the invention using species specific CD154 polypeptides or a heterologous CD154 polypeptide.

In another alternative, the CD40 ligand may be a CD40 agonistic antibody or portion thereof. Such CD40 agonistic antibodies are disclosed at least in International Application No. WO2015/187969. CD40 antibodies and agonisitic CD40 antibodies are also commercially available for several species, in particular mouse and human. An antibody is agonistic for CD40 if it is capable of inducing signaling within the target cell expressing CD40. The signalling via CD40 results in increased expression of CD40 and TNF receptors on the surface of the antigen-presenting cells and induces production of reactive oxygen species and nitric oxide, and B cell activation leading to isotype switching.

Suitable chicken CD40 agonistic antibodies include the antibody provided herein as SEQ ID NO: 113 (heavy chain) and SEQ ID NO: 114 (light chain) referred to as 2C5 or SEQ ID NO: 115 (single chain variable fragment (scFv)) referred to as DAG-1). These antibodies may be made in a "chick-enized" form such that the Fc portion and the non-CDR regions may be replaced with homologous host-compatible antibody backbone sequences to minimize the immune response to the antibody backbone itself. In addition, the antibodies may be made either recombinantly or via enzyme digestion (i.e. papain or pepsin) into smaller portions of the antibodies and include only the F(ab) portion of the antibody, such as an $F(ab)_2$ fragment. The CDR regions for both chicken CD40 antibodies have been identified. For the antibody designated as 2C5 and provided in SEQ ID NO: 113 and SEQ ID NO: 114, the heavy chain variable region comprises a CDR1 comprising the amino acid sequence set forth in SEQ ID NO: 116, a CDR2 comprising the amino acid sequence set forth in SEQ ID NO: 117, and a CDR3 comprising the amino acid sequence set forth in SEQ ID NO: 118 and the light chain variable region comprises a CDR1 comprising the amino acid sequence set forth in SEQ ID NO: 119, a CDR2 comprising the amino acid sequence set forth in SEQ ID NO: 120, and a CDR3 comprising the amino acid sequence set forth in SEQ ID NO: 121. For the antibody designated as DAG-1 and provided in SEQ ID NO: 115, the heavy chain variable region comprises a CDR1 comprising the amino acid sequence set forth in SEQ ID NO: 122, a CDR2 comprising the amino acid sequence set forth in SEQ ID NO: 123, and a CDR3 comprising the amino acid sequence set forth in SEQ ID NO: 124 and wherein the light chain variable region comprises a CDR1 comprising the amino acid sequence set forth in SEQ ID NO: 125, a CDR2 comprising the amino acid sequence set forth in SEQ ID NO: 126, and a CDR3 comprising the amino acid sequence set forth in SEQ ID NO: 127. Also included are polypeptides identical to, or at least 99% identical, at least 98% identical, at least 95% identical, at least 90% identical, at least 85% identical, or at least 80% identical to at least one of SEQ ID NOs: 113-127.

The vaccine compositions provided herein comprise a yeast. The yeast may be selected from any of the following yeast genus: *Saccharomyces, Candida, Cryptococcus, Hansenula, Kluyveromyces, Pichia, Rhodotorula, Schizosaccharomyces* and *Yarrowia*. The yeast may be of a species selected from the group consisting of *Saccharomyces cerevisiae, Candida albicans, Hansenula polymorpha, Pichia pastoris* and *Schizosaccharomyces pombe*. In the Examples *Pichia pastoris* was used. The yeast include an immunostimulatory polynucleotide encoding an immunostimulatory polypeptide and may further comprise an antigenic polynucleotide encoding an antigenic polypeptide. Suitably the immunostimulatory polypeptide and the antigenic polypeptide are not natively expressed by the yeast. The yeast are engineered to express the immunostimulatory polypeptide and the antigenic polypeptide and display or express these polypeptides on the surface of the yeast.

At least a portion of the antigenic polypeptide and at least a portion of the immunostimulatory polypeptide are present on the surface of the *Pichia pastoris* or other yeast-based vaccine composition. Present on the surface of the vaccine composition includes polypeptides that are comprised within a transmembrane protein, interacting with, covalently or chemically cross-linked to a transmembrane protein, a membrane lipid or membrane GPI-anchored carbohydrate or protein. A polypeptide can be comprised within a transmembrane protein by having the amino acids comprising the polypeptide linked via a peptide bond to the N-terminus, C-terminus or anywhere within the transmembrane protein (i.e. inserted between two amino acids of the transmembrane protein or in place of one or more amino acids of the transmembrane protein (i.e. deletion-insertion)). Those skilled in the art will appreciate that a non-native immunostimulatory polynucleotide or an antigenic polynucleotide may be inserted in frame within an extracellular loop of a transmembrane or cell wall protein to obtain surface expression of the immunostimulatory or antigenic polypeptide. In the Examples, the α-agglutinin C-terminal anchoring method that uses a covalently linked GPI-anchoring system of yeast is used, but other similar anchoring methods are available to those of skill in the art.

Alternatively, the polypeptides may be covalently or chemically linked to proteins, lipids or carbohydrates in the membrane through methods available to persons of skill in the art. For example, di-sulfide bonds or biotin-avidin cross-linking could be used to present the antigenic and immunostimulatory polypeptides on the surface of a yeast in the vaccine compositions. Suitably, the antigenic polypeptide and the immunostimulatory polypeptide are part of a fusion protein. The two polypeptides may be directly linked via a peptide bond or may be separated by a linker peptide encoded by a polynucleotide or a section of a third protein into which they are inserted. In some embodiments a fusion protein comprising more than one copy of each of the immunostimulatory polypeptide and/or the antigenic polypeptide is included in the yeast. In some embodiments, the multiple copies of the immunostimulatory polypeptide include more than one copy of the same immunostimulatory polypeptide or different polypeptides. The same is true for the antigenic polypeptides in that multiple copies of the same or analogous antigenic polypeptides may be included in the yeast, e.g., multiple copies of the avian influenza M2e antigen possibly having single or only a few amino acid sequence differences. Alternatively the yeast may be engineered to express multiple different and distinct antigenic polypeptides to allow for a single administration of a vaccine composition to elicit or enhance the immune response to different antigens from different species. For example, the vaccine composition may be prepared to enhance the immune response to subsequent infection with *Campylobacter* and *Eimeria* by including antigenic polypeptides of SEQ ID NO: 55 and SEQ ID NO: 61 may be included in the same vaccine composition.

Polynucleotides encoding the antigenic polypeptide or immunostimulatory polypeptides may be inserted into the yeast of the vaccine composition and expressed to generate the antigenic polypeptide and the immunostimulatory polypeptide. The polynucleotides may be inserted into the chromosome of the vaccine composition or encoded on plasmids or other extrachromosomal DNA such as on a YAC (yeast artificial chromosome). Suitably, polynucleotides encoding the antigenic polypeptide and/or the immunostimulatory polypeptide may be expressed independently or are inserted into a yeast vaccine polynucleotide that is expressed. The yeast vaccine polynucleotide may encode a polypeptide expressed on the surface of the yeast vaccine such as a transmembrane protein. The polynucleotide encoding the antigenic polypeptide and/or the immunostimulatory polypeptide may be inserted into the yeast vaccine polynucleotide sequence to allow expression of the antigenic polypeptide and/or the immunostimulatory polypeptide on the surface of the yeast.

Alternatively, the polynucleotide encoding the antigenic polypeptide and/or the immunostimulatory polypeptide may be inserted into a secreted polypeptide which is displayed or presented on the surface of the yeast vaccine through association with a protein, lipid or carbohydrate on the surface of the yeast vaccine. Those of skill in the art will appreciate that the polynucleotide encoding the antigenic polypeptide and/or the immunostimulatory polypeptide could be inserted in a wide variety of yeast polynucleotides to provide expression and presentation of the antigenic polypeptide and/or the immunostimulatory polypeptide to the immune cells of a subject treated with the yeast.

As noted in the discussion above, the vaccines described herein may also include an antigenic polynucleotide encoding an antigenic polypeptide. An antigenic polypeptide is a polypeptide that is capable of being specifically recognized by the adaptive immune system. The antigenic polypeptide may be natively expressed by the yeast chosen as the vector to vaccinate against the yeast acting as the vaccine vector. Alternatively, a yeast vaccine vector may carry a heterologous polynucleotide encoding a heterologous polypeptide not natively associated with the vaccine vector as the antigenic polypeptide. An antigenic polypeptide includes any polypeptide that is immunogenic. The antigenic polypeptides include, but are not limited to, antigens that are pathogen-related, allergen-related, tumor-related or disease-related. Pathogens include viral, parasitic, fungal and bacterial pathogens as well as protein pathogens such as the prions. The antigenic polypeptides may be full-length proteins or portions thereof.

It is well established that immune system recognition of many proteins is based on a relatively small number of amino acids, often referred to as the epitope. Epitopes may be only 8-10 amino acids. The term antigenic polypeptide may include an epitope to which an antibody or T cell immune response is generated in the subject. The term epitope and antigen or antigenic polypeptide may be used interchangeably. Thus, the antigenic polypeptides described herein may be full-length proteins, 8 amino acid long epitopes or any portion between these extremes. In fact the antigenic polypeptide may include more than one epitope from a single pathogen or protein. Antigenic polypeptides may include but will not be limited to large segments of bacteria or small polypeptides of bacteria such as those associated with Mastitis infection, *Salmonella, Clostridium, Campylobacter, Escherichia, Shigella, Helicobacter, Vibrio, Plesiomonas, Edwardia, Klebsiella, Staphylococcus, Streptococcus, Aeromonas*; viral proteins including but not limited to influenza, Foot and Mouth virus, porcine epidemic diarrhea virus (PEDv), and Porcine reproductive and respiratory syndrome virus (PRRSV); parasitic infections including but not limited to *Eimeria* spp, *Toxoplasma*, malaria, or other parasites; and tumor antigens. For example, the antigens or epitopes identified in U.S. Pat. No. 8,604,198, International Publication Nos. WO2009/059018, WO2009/059298, WO2011/091255, WO2011/156619, WO2014070709, WO 2014/127185 or WO 2014/152508 may be used. Antigenic polypeptides may include any one or more of those provided in SEQ ID NOs: 39-93 and include polypeptides identical to, or at least 99% identical, at least 98% identical, at least 95% identical, at least 90% identical, at least 85% identical, or at least 80% identical to those provided in SEQ ID NOs: 39-93. Those skilled in the art recognize that some of the peptides included in SEQ ID NO: 39-93 are longer than is likely required to act as an antigenic epitope, thus fragments of these antigenic polypeptides are also included herein. Those skilled in the art will also recognize that the antigenic polypeptides may also include additional amino acids or may be linked to each other or to the immunostimulatory polypeptide via linker amino acids to form a sort of fusion protein. The linker amino acids may be any amino acids but serine and glycine are most commonly used. The linker may be as short as one or two amino acids, but may be 4, 5, 6, 8, 10, 12, 14, 15 or more amino acids long.

Multiple copies of the same epitope or antigenic polypeptide or multiple epitopes from different proteins may be included in the vaccine vector. It is envisioned that several epitopes or antigens from the same or different pathogens or diseases may be administered in combination in the yeast vaccine vector to generate an enhanced immune response against multiple antigens. The yeast vaccine vector may encode antigens from multiple pathogenic microorganisms, viruses or tumor associated antigens. Administration of vaccine vectors capable of expressing multiple antigens has the advantage of inducing immunity against two or more diseases at the same time.

The polynucleotide encoding an immunostimulatory polypeptide capable of enhancing the immune response to an antigenic polypeptide may also encode the antigenic polypeptide. The polynucleotide encoding an immunostimulatory polypeptide may be linked to the polynucleotide encoding the antigenic polypeptide, such that in the vaccine vector the immunostimulatory polypeptide and the antigenic polypeptide are encoded by the same polynucleotide. At least a portion of the antigenic polypeptide and the immunostimulatory polypeptide are present on the surface of the yeast vaccine vector. The vaccine composition may include an antigenic polynucleotide encoding the antigenic polypeptide and an immunostimulatory polynucleotide encoding the immunostimulatory polypeptide. The immunostimulatory polypeptide and the antigenic polypeptide may be linked, such as in a fusion protein. The immunostimulatory polypeptide and the antigenic polypeptide may both be inserted within an external loop of a transmembrane protein or may be attached to the surface through a GPI-anchoring mechanism.

Heterologous polynucleotides include, but are not limited to, polynucleotides encoding antigens selected from pathogenic microorganisms or viruses other than the yeast vaccine vector. Such heterologous or antigenic polynucleotides may be derived from pathogenic viruses such as influenza (e.g., M2e, hemagglutinin, or neuraminidase), herpesviruses (e.g., the genes encoding the structural proteins of herpesviruses), retroviruses (e.g., the gp160 envelope protein), adenoviruses, paramyxoviruses, coronaviruses and the like. Heterologous polynucleotides can also be obtained from pathogenic bacteria, e.g., genes encoding bacterial proteins such as toxins, and outer membrane proteins. Further, heterologous polynucleotides from parasites, such as *Eimeria* are attractive candidates for use in a yeast vectored vaccine composition.

Additional immunostimulatory polypeptides involved in triggering the immune system may also be included in the vaccine compositions described herein. The polynucleotides may encode immune system molecules known for their stimulatory effects, such as an interleukin, Tumor Necrosis Factor or an interferon, or another polypeptide involved in immune-regulation such as a CD40 ligand or CD40 agonist. Thus the yeast vaccine vectors may contain more than one immunostimulatory polypeptide or more than one antigenic polypeptide. This includes more than one copy of the same polypeptide to increase the expression level of the polypeptide. Alternatively multiple different immunostimulatory polypeptides or nucleotides encoding the same or multiple antigenic polypeptides or nucleotides encoding the same may be included in a single recombinant yeast. The multiple antigenic polypeptides may be multiple copies of a similar antigen such as two different epitopes of the M2e antigen (SEQ ID NO: 41 and 42). The antigenic polypeptides may be antigens directed to completely different antigens but related to the same infectious agent such as M2e and HAS. See SEQ ID NOs: 41-44. The antigenic polypeptides may also be antigens directed to different species in order to vaccinate against more than one pathogen with a single unitary vaccine. Such as SEQ ID NO: 41 to Influenza M2e in combination with SEQ ID NO: 54 directed to PAL from *E. coli* or SEQ ID NO: 61 directed to MPP from *Eimeria*. In the Examples, a vaccine composition comprising a yeast expressing MPP-TRAP-HMGB-1 (SEQ ID NO: 61 linked to SEQ ID NO: 65 linked to SEQ ID NO: 2) was generated and shown to reduce both morbidity and mortality associated with challenge with *Eimeria maxima*.

Compositions comprising the vaccine compositions and a pharmaceutically acceptable carrier are also provided. A pharmaceutically acceptable carrier is any carrier suitable for in vivo administration. Suitably, the pharmaceutically acceptable carrier is acceptable for oral, nasal or mucosal delivery. The pharmaceutically acceptable carrier may include water, buffered solutions, glucose solutions or bacterial culture fluids. Additional components of the compositions may suitably include excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying.

The vaccine compositions may not be capable of replication in the subject. The yeast may be incapable of growth outside of a laboratory environment, such as an attenuated form of the yeast. Suitably the yeast is inactivated or killed prior to addition to the vaccine composition. The vaccine compositions may also include an adjuvant. Adjuvants are known in the art and in the Examples a mannosylated chitosan adjuvant was used. See WO 2014/070709.

The compositions described herein may be used to enhance an immune response such as an antibody response to the antigenic polypeptide or to the vaccine vector itself. The compositions and vaccine vectors described herein may reduce the severity of subsequent disease by decreasing the length of disease, decreasing the morbidity or mortality associated with the disease or reducing the likelihood of contracting the disease. The morbidity or mortality associated with the disease after administration of the vaccine vectors described herein may be reduced by 25%, 30%, 40%, 50%, 60%, 70%, 80%, 90% or even 100% as compared to similar subjects not provided the vaccine vector.

Methods of enhancing immune responses in a subject by administering the vaccine composition are also provided. The vaccine composition may contain a full length immunostimulatory polypeptide or portion thereof capable of stimulating the immune response to the vaccine composition and its associated antigenic polypeptide. The vaccine composition comprising an immunostimulatory polypeptide is administered to a subject in an amount effective to enhance the immune response of the subject to the vaccine and in particular to the antigenic polypeptide. Enhancing an immune response includes, but is not limited to, inducing a therapeutic or prophylactic effect that is mediated by the immune system of the subject. The effect may be measured by testing a response to the antigenic polypeptide or to an infectious or cancerous agent that expresses the antigenic polypeptide. Specifically, enhancing an immune response may include, but is not limited to, enhanced production of antibodies, enhanced class switching of antibody heavy chains, maturation of antigen presenting cells, stimulation of helper T cells, stimulation of cytolytic T cells or induction of T and/or B cell memory.

The compositions may be administered by a variety of means including, but not limited to, subcutaneously, orally, intranasally, and mucosally. For example, the vaccine compositions or vaccine vectors may be delivered by aerosol, by spraying, by addition to food or water, by oral gavage, or via eye drops. In some embodiments, the compositions are administered by injection such as intradermally, parenterally, subcutaneously, intraperitoneally, intravenously, intracranially, or intramuscularly. For chickens or other poultry, the compositions may be administered in ovo. Combinations of administration means may also be used. In the Examples a sub-cutaneous vaccination was followed by a boost of the vaccine composition given orally. Other combinations may also be used, such as intranasal or delivery via aerosols or spraying followed by oral gavage or inclusion in the feed or drinking water.

Subjects include, but are not limited to, a vertebrate, suitably a mammal, suitably a human, cows, cats, dogs, pigs, aquaculture, suitable catfish, snapper, goldfish, or birds, suitably poultry such as chickens or turkeys. Other animal models of infection may also be used. Enhancing an immune response includes, but is not limited to, inducing a therapeutic or prophylactic effect that is mediated by the immune system of the subject. Specifically, enhancing an immune response may include enhanced production of antibodies, such as demonstrated in FIGS. 4 and 5. In some embodiments, an IgA response is produced.

The useful dosage to be administered will vary depending on the age, weight and species of the subject, the mode and route of administration and the type of pathogen or disease against which an immune response is sought. The composition may be administered in any dose of yeast vaccine vector sufficient to evoke an immune response. It is envisioned that doses ranging from $10^5$ to $10^{10}$ yeast vector copies are sufficient. Specifically, the dosage of $10^8$ *Pichia pastoris*-HMGB1 vaccine vector copies determined by counting the number of yeast in a cubic mm using a hemacytometer under 400× magnification was optimal for inducing a vaccine vector specific immune response ultimately signifying stimulation of an immune response to antigenic cargo adjacent to HMGB1 on the yeast cell surface.

The composition may be administered only once or may be administered two or more times to increase the immune response. If the composition is administered more than one time, the composition may be administered via different routes of administration each time the vaccine is administered as discussed above. For example, the composition may be administered two or more times separated by one week, two weeks, or by three weeks, one month, two months, three months, six months or more. The yeast may be viable prior to administration, but in most embodiments the yeast will be killed or inactivated prior to administration. In some embodiments, the yeast may be able to replicate in the subject, while in other embodiments the yeast may not be capable of replicating in the subject. As shown in the Examples, the yeast vaccine vector may be inactivated prior to administration using formalin, glutaraldehyde, ethanol, acidification, heat or antibiotics. One skilled in the art would appreciate other means of inactivating yeast vaccine vectors could be used as well.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

We have developed a *Pichia pastoris* vaccine vector that expresses full length high mobility group box 1 (HMGB1) to significantly increase the immune response to antigenic cargo. Previously, we inserted a truncated CD154, or CD40 ligand, polypeptide and/or full length HMGB1 into a double attenuated *Salmonella Enteriditis* (SE) and compared phagocytic uptake of the SE by Raw 264 murine macrophage cells (FIG. 1). Relative fluorescence intensity within Raw 264 was measured using fluorescence activated cell sorting (FACS) analysis. The fluorescence intensity was measured because the fluorescence signal on the *S. aureus* pHrodo particles increases at a more acidic pH. A phagolysosome is created within the macrophage once the bacteria are taken into the macrophage by phagocytosis. The macrophage breaks down bacteria by acidifying the pH inside of a phagolysosome. Therefore, the macrophages that were actively breaking down bacteria would have greater fluorescence intensity. The data in FIG. 1 demonstrate that murine macrophages preferentially phagocytosed the SE vaccine vector containing HMGB1 as compared to the attenuated SE vaccine vector alone (P=0.011) and CD154 did not significantly alter phagocytic uptake by murine macrophages (P=0.057).

Figure 2:
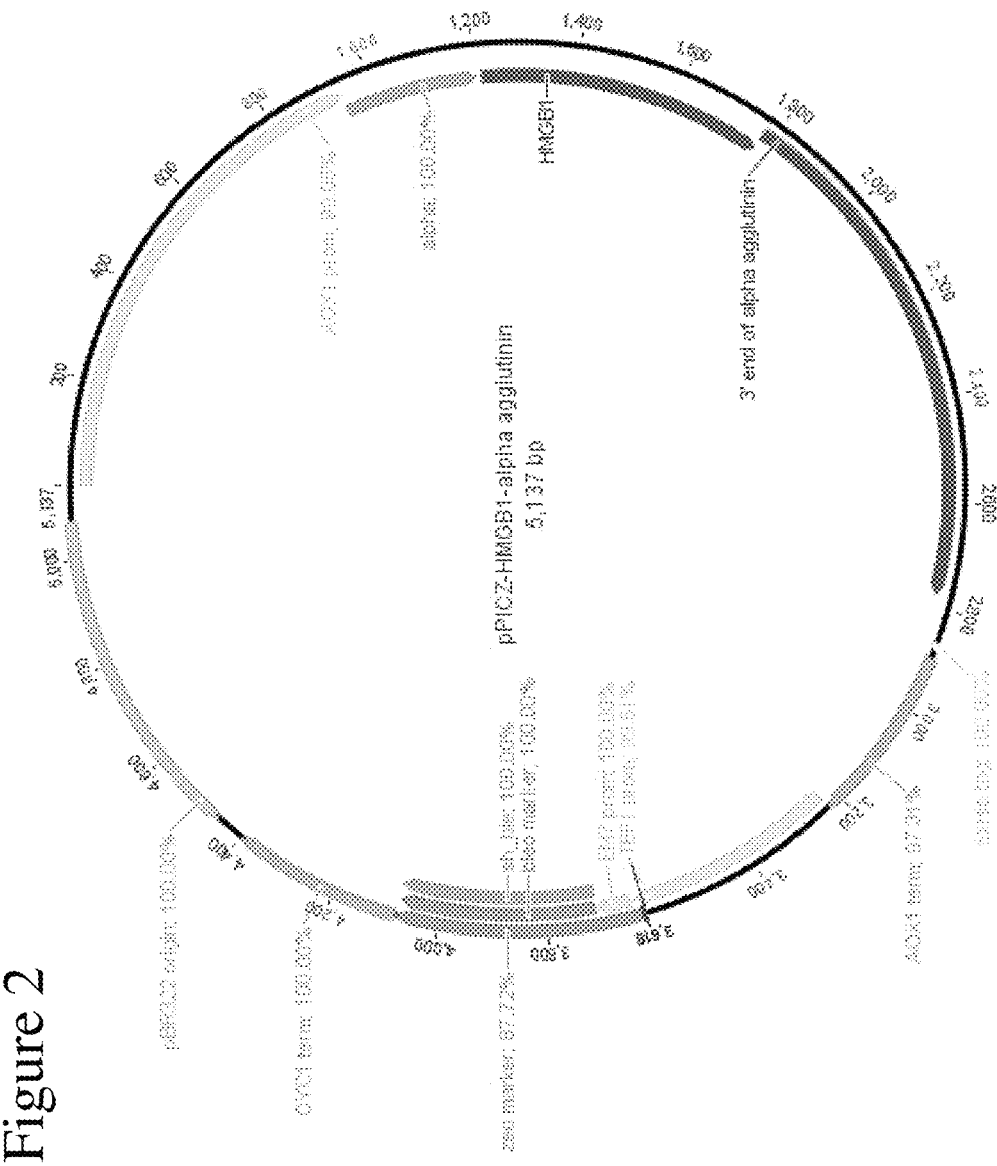
FIG. 2 is a schematic depiction of the pPICZ plasmid map engineered to include *Gallus gallus* specific high mobility group box 1 (HMGB1) protein expression on the *Pichia pastoris* using the glycosylphosphatidylinositol anchored *Saccharomyces cerevisiae* alpha agglutinin cell surface expression method. pPICZ is methanol inducible using the AOX1 promoter.

We have engineered *Pichia pastoris* for cell surface expression of HMGB1 using a plasmid integrated system to chromosomally insert the HMGB1 protein into *Pichia pastoris* increasing the immune response to the vaccine cargo. *Pichia pastoris* yields 10- to 100-fold higher protein expression than *Saccharomyces cerevisiae*. HMGB1 sends a danger signal to the immune system triggering the RAGE response. The phagocytosis assay described above shows that HMGB1 is a potent immune stimulatory molecule that can increase uptake of the carrier system, for example, *Salmonella Enteriditis*, into murine macrophages. HMGB1 expression on the cell surface of the yeast should enhance uptake of the yeast-vectored vaccine into macrophages by phagocytosis as observed in the *Salmonella Enteriditis* construct. We obtained an EasySelect *Pichia* Expression Kit from Invitrogen® that includes the pPICZ expression vector for expression in *Pichia pastoris*. A cell surface expression kit for *Pichia pastoris* is not currently available, but several researchers have used GPI-anchored proteins to initiate cell surface expression in a yeast system (Wasilenko et al., 2009). The GPI-anchored protein that was used is the C-terminus portion of the α-agglutinin from *Saccharomyces cerevisiae*. HMGB1 connected to the C-terminus portion of *Saccharomyces cerevisiae* α-agglutinin by a serine spacer region was spliced into the pPICZ intracellular expression plasmid (FIG. 2 and SEQ ID NO: 1). pPICZ is a methanol inducible plasmid for fast and high levels of protein expression. Cell surface expression of HMGB1 was confirmed in FIGS. 3A-3F, which shows immunofluorescence of the presence of HMGB-1 only on the transformed yeast cells (FIG. 3E and FIG. 3F).

Figure 4:
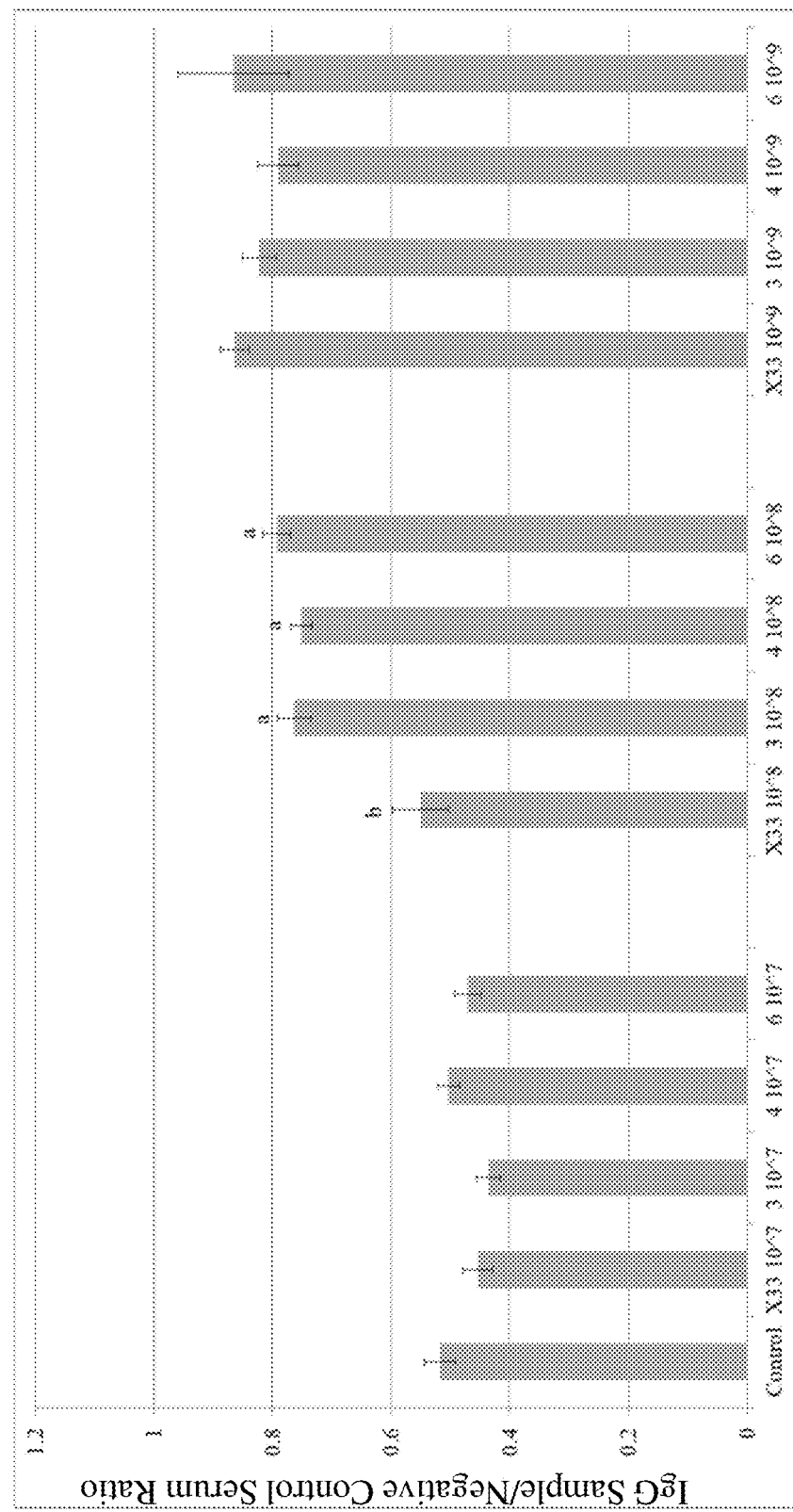
FIG. 4 is a graph showing the *Pichia pastoris* specific serum antibody sample/negative control serum ratio. We observed a typical dose response curve of *Pichia pastoris* specific antibodies determined using an ELISA. *Pichia pastoris* administered SQ at $10^7$/broiler was too little to mount an immune response, and $10^9$/broiler was too much resulting in seroconversion to even the X33 construct backbone. *Pichia pastoris* administered SQ at $10^8$/broiler was the best dose that resulted in all HMGB1+*Pichia pastoris* constructs significantly elevating *Pichia pastoris* specific serum antibodies (P<0.001).

After HMGB1 protein expression confirmation on the cell surface of *Pichia pastoris*, we chose three HMGB1 positive *Pichia pastoris* clones to test in broiler chickens (n=15 chicks/group). The *Pichia pastoris*-HMGB1 positive clones #3, 4, and 6 were inactivated using 0.3% glutaraldehyde in sterile water and mixed 1:2 in mannosylated chitosan adjuvant. See WO 2014/070709 which is incorporated herein by reference in its entirety. We administered three doses, $10^7$-$10^9$, of each *Pichia pastoris*-HMGB1 positive construct by subcutaneous injection, 0.25 mL of vaccine/chick (Table 1). Broiler chicks were vaccinated on day of hatch and on day 14. Serum was collected for IgG antibody titer measurement on day 21. A direct ELISA measuring IgG specific for *Pichia pastoris* was optimized in our laboratory. Sample/negative control serum ratios were reported to account for plate to plate variability within the ELISA assay. Antibody titers specific for *Pichia pastoris* were determined from each broiler chick. *Pichia pastoris*-HMGB1 vaccinated chicks' IgG were compared to non-modified *Pichia pastoris* (X33) vaccinated chicks' IgG. The results are shown in FIG. 4.

TABLE 1

*Pichia pastoris* vaccination dose strategy in broiler chicks

| | Group | Dose |
|---|---|---|
| 1 | Control-No *Pichia pastoris* | — |
| 2 | *Pichia pastoris* w/o HMGB1 (X33) | $10^7$ |
| 3 | *Pichia pastoris*-HMGB1 3 | $10^7$ |
| 4 | *Pichia pastoris*-HMGB1 4 | $10^7$ |
| 5 | *Pichia pastoris*-HMGB1 6 | $10^7$ |
| 6 | *Pichia pastoris*-HMGB1 (X33) | $10^8$ |
| 7 | *Pichia pastoris*-HMGB1 3 | $10^8$ |
| 8 | *Pichia pastoris*-HMGB1 4 | $10^8$ |
| 9 | *Pichia pastoris*-HMGB1 6 | $10^8$ |
| 10 | *Pichia pastoris*-HMGB1 (X33) | $10^9$ |
| 11 | *Pichia pastoris*-HMGB1 3 | $10^9$ |
| 12 | *Pichia pastoris*-HMGB1 4 | $10^9$ |
| 13 | *Pichia pastoris*-HMGB1 6 | $10^9$ |

We then vaccinated three-week-old broiler chickens with the *Pichia pastoris*-HMGB1 constructs #3, 4, or 6 to determine whether a similar IgG antibody response would be observed. We vaccinated three-week-old broiler chickens with 0.25 mL of each *Pichia pastoris* vaccine (Table 1: n=10 chickens/group). The *Pichia pastoris*-HMGB1 positive constructs #3, 4, or 6 were inactivated using 0.3% glutaraldehyde in sterile water and mixed 1:2 in mannosylated chitosan adjuvant. Broiler chickens were vaccinated on day 21 and on day 35. Serum was collected for IgG antibody titer measurement on day 21. A direct ELISA measuring IgG specific for *Pichia pastoris* was optimized in our laboratory. Absorbance at 450 nm normalized for non-vaccinated chickens (group 1) were reported to account for plate to plate variability within the ELISA assay. Antibody titers specific for *Pichia pastoris* were determined from each broiler chick. *Pichia pastoris*-HMGB1 vaccinated chicks' IgG were compared to non-modified *Pichia pastoris* (X33) vaccinated chicks' IgG. The results are depicted in FIG. 5.

Figure 5:
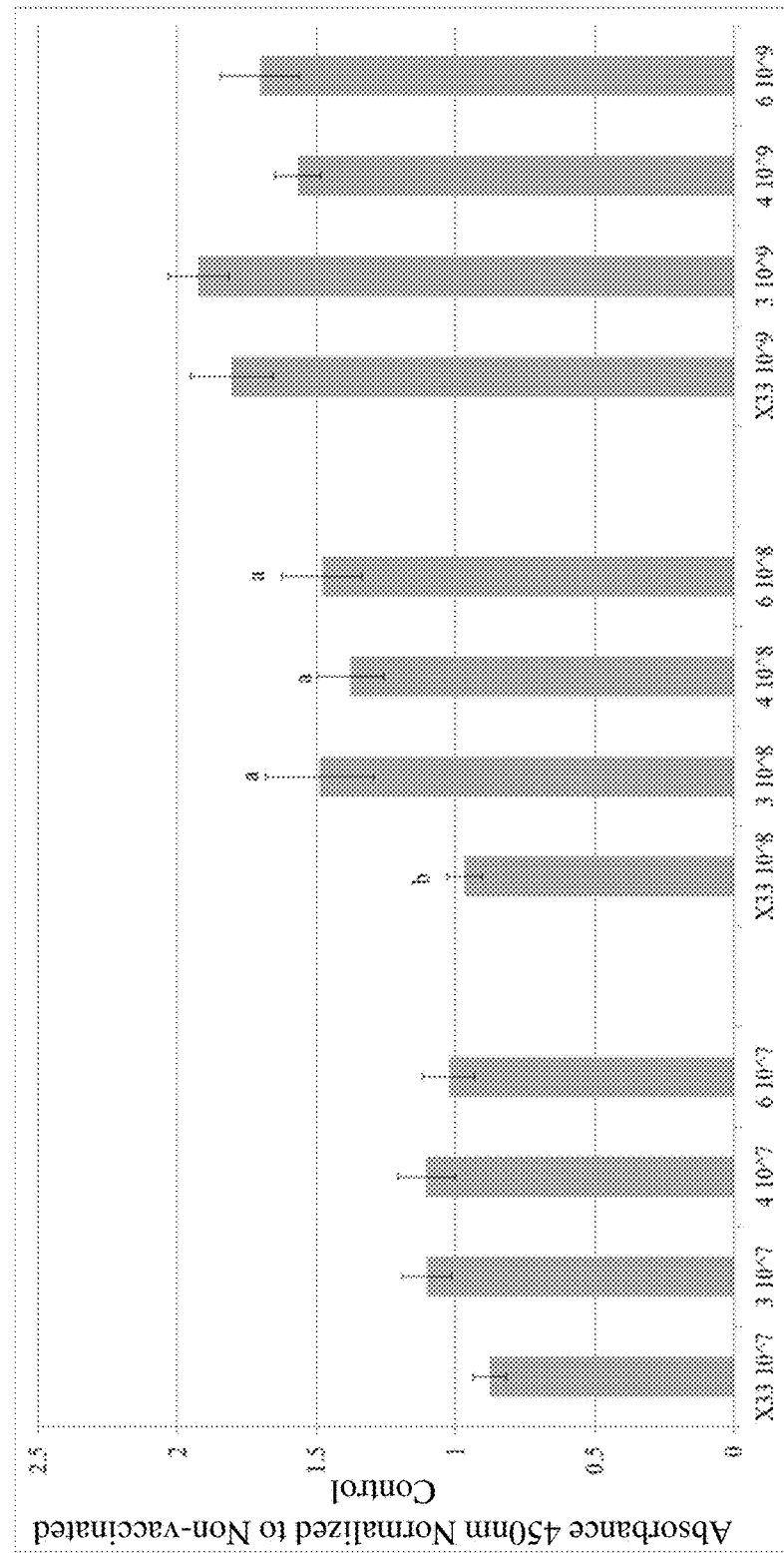
FIG. 5 is a graph showing the *Pichia pastoris* specific serum antibody normalized to non-vaccinated control broilers (Group 1) serum ratio. The dose response that we expected repeated. We observed a typical dose response curve. *Pichia pastoris* administered SQ at $10^7$/broiler was too little to mount an immune response, and $10^9$/broiler was too much resulting in seroconversion to even the X33 construct backbone. *Pichia pastoris* administered SQ at $10^8$/broiler was the best dose that resulted in all HMGB1+ *Pichia pastoris* constructs significantly elevating *Pichia pastoris* specific serum antibodies (P=0.049).

HMGB1 significantly elevated IgG antibody titers specific for *Pichia pastoris* in broilers injected SQ with inactivated HMGB1+*Pichia pastoris* as compared to those injected with non-modified *Pichia pastoris* (FIG. 4 and FIG. 5). HMGB1 increased the immune response to the *Pichia pastoris* vaccine vector suggesting that any antigenic cargo expressed by the same *Pichia pastoris* would elicit a higher immune response than if the antigenic cargo were expressed in *Pichia pastoris* without HMGB1.

Materials and Methods

*Pichia pastoris* X-33 (wild type) was obtained from Invitrogen (Carlsbad, Calif., USA) as part of the Easy Select™ *Pichia* Expression Kit. The HMGB1 coding sequence-optimized for expression in *Pichia pastoris*-was synthesized by Genscript (Piscataway, N.J., USA), and supplied to our lab in a pUC57 cloning vector. TOP10 electrocompetent *E. coli* (Invitrogen) was used for all necessary plasmid propagation during vaccine construction. Following transformations with plasmid DNA, *E. coli* was propagated at 37° C. using either LB medium supplemented with 100 µg/mL Ampicillin, or low salt LB medium containing 50 µg/mL Zeocin. Routine propagation of *Pichia pastoris* was done at 30° C. using YPD medium supplemented with 50 µg Zeocin when appropriate. Minimal medium for yeast containing histidine (MMH) and minimal medium for yeast containing dextrose (MDH) were used for subsequent screening of the recombinant vaccine strains. Minimal medium containing glycerol (MGY) and minimal medium containing methanol (MM) were used to induce expression of HMGB1 from *Pichia pastoris* in cultures.

Construction of Vaccine Vector.

To make the *Pichia pastoris*-HMGB1 expression vector, pPICZ was digested with KpnI and PmeI to prepare the vector backbone for cloning. pUC57/HMGB1-alpha agglutinin was digested with KpnI and EcoRV and the 1.6 kb HMGB1-alpha agglutinin insert was subsequently gel purified. Following ligation and transformation into TOP10 *E. coli*, colony PCR was performed to identify colonies carrying the proper pPICZ/HMGB1-alpha agglutinin ligated plasmid. Primers for this PCR-AOXSeqF (5' GACTGGTTC-CAATTGACAAGC 3'; SEQ ID NO: 128); AOXSeqR (5' GCAAATGGCATTCTGACATCC 3'; SEQ ID NO: 129) were provided in the Easy Select™ kit. Amplicons were produced using KOD DNA polymerase (Millipore; Darmstadt, Germany). Cycling parameters for this reaction are as follows: 98° C., 10 minutes; followed by 25 cycles of 98° C., 15 seconds; 55° C., 5 seconds. The ligated plasmid pPICZ/HMGB1-alpha agglutinin was further verified with sequencing at the University of Arkansas DNA core laboratory facility (Fayetteville, Ark.). pPICZ/HMGB1-alpha agglutinin was subsequently linearized via PmeI digestion and purified to prepare for electroporation in to *Pichia pastoris* X-33.

For electroporation, 5 mL of *Pichia pastoris* X-33 was grown overnight at 30° C. in YPD broth. Five hundred milliliters of fresh YPD broth was inoculated the following day with the 5 mL culture and grown to an OD of 1.5. Cells were then washed twice with ice-cold, sterile water and once with ice-cold, sterile sorbitol (1M). Cells were ultimately resuspended in 1 mL of ice-cold sorbitol. Eighty microliters of the competent *Pichia pastoris* was mixed with 10 µg of linearized pPICZ/HMGB1-alpha agglutinin and pulsed once at 2.0 KV to electroporate the yeast cells. Transformants that underwent successful chromosomal integration of the linear vaccine construct containing the Zeocin resistance gene were selected on YPD plates containing 100 μg/mL Zeocin. Again, colony PCR was used to analyze the transformants. The aforementioned primers and cycling parameters were utilized.

Screening of *Pichia pastoris* pPICZ/HMGB1 AOX1 Gene.

Resulting vaccine strains were tested to verify the presence and stability of the AOX1 gene needed to drive expression of HMGB1-alpha agglutinin. Nine Zeocin resistant strains in addition to GS115 Mut⁻ (a negative control strain with a nonfunctional AOX1 gene provided in the Easy Select™ *Pichia* Expression Kit) were tested by plating on MDH and MMH agar. AOX1 deficient strains show much slower growth on MMH medium than on MDH. Growth times on these two mediums are used to identify AOX1 deficient strains. Each of the nine strains plus the negative control GS115 Mut⁻ were replica plated on MMH and MDH mediums and incubated for 3 days. Cultures were checked every 24 hours and levels of growth were recorded.

HMGB1-Alpha Agglutinin Protein Induction.

To induce expression of HMGB1 in culture, a 50 mL *Pichia pastoris* pPICZ/HMGB1-alpha agglutinin culture was grown overnight at 30° C. in MGY broth from a single colony. Twenty-five milliliters of this overnight culture was transferred into 250 mL or pre-warmed MM broth and covered with sterilized cheese-cloth for proper aeration. This culture was then grown with vigorous shaking (250 rpm) for 96 hours; with 100% methanol being added to a final concentration of 0.5% every 24 hours to maintain induction. Induction of the HMGB1-alpha agglutinin gene product was maximized after 96 hours.

After induction, each of the nine *Pichia pastoris*-HMGB1 positive constructs were tested for HMGB1 protein expression on the *Pichia pastoris* cell surface using an immunofluorescence assay. *Pichia pastoris*-HMGB1 construct #1, 3, 4, 5, 6, 7, 8, 9, and 10 and X33 backbone were stained using rabbit polyclonal HMGB1 156-177 diluted 1:5 in phosphate buffered saline (PBS) with the $F(ab)^2$ portion of goat anti-rabbit IgG conjugated with ALEXA 488® at 1:1000 in 1% goat serum in PBS. HMGB1 protein expression was optimally expressed on three (#3, 4, and 6) of the nine *Pichia pastoris*-HMGB1 constructs that were transformed (FIGS. 3A-3F).

Evaluation of *S. Enteritidis* Recovery after Vaccination with a Yeast Vectored Vaccine Candidate.

We next tested the efficacy of Yeast vectored PAL-HMGB1 (SEQ ID NO: 54 linked to SEQ ID NO: 2) and antibody guided PAL vaccine candidates to reduce recovery of S. *Enteritidis* (SE), a serogroup D *Salmonella*, after challenge. Sixty SPF leghorn chicks were hatched at the poultry farm. On the day of hatch, chicks were divided into two groups, control or vaccinated. Vaccinated chicks were vaccinated with $4.25\times10^9$ cfu/bird Yeast-PAL-HMGB1 subcutaneously and by oral gavage, both groups were then placed in batteries with wire floors, and feed and water were provided ad libitum. Prior to vaccination, ten 1-day-old chicks were euthanized by $CO_2$ inhalation for sampling to confirm the chicks were *Salmonella* negative. On day 7, vaccinated chickens were boosted with $5\times10^9$ cfu/bird subcutaneously and by oral gavage. On day 14, all chickens were challenged by oral gavage with $1.2\times10^8$ cfu/bird SE. On days 21 and 28, 10 cloacal swabs per group were obtained to assess shedding of challenge strains. On days 32, liver and spleen (LS), and ceca (CT) were collected from 20 chickens (control) or 10 chickens (vaccinated) and cultured by direct plating (CFU/g) and enrichment for SE incidence. Summary of experimental procedure:

| Group No. (n = 30) | Group | Vaccination Dose DOH | Boost Dose D 7 | Challenge Dose D 14 | Cloacal Swabs |
|---|---|---|---|---|---|
| 1 | Control | NA | NA | SE@$10^8$/bird | D 21, 28 |
| 2 | Yeast-PAL-HMGB1-SC/oral | $10^9$/ml | $10^9$/ml | SE@$10^8$/bird | D 21, 28 |

As shown in Table 2, significantly less *Salmonella* was recovered from chickens vaccinated with the Yeast-PAL-HMGB-1 vaccine by 18 days post-challenge. As shown in Table 3, significantly less *Salmonella* was also recovered from cloacal swabs and was completely cleared as early as 2 weeks post-challenge.

TABLE 2

Recovery of SE 18 days post-challenge.

| | LS (% +) | CT (% + (# +)) |
|---|---|---|
| Control | 0 | 65 (13/20) |
| Yeast-PAL-HMGB1 | 0 | 30 (3/10)* |

*Different from Control $p < 0.1$

TABLE 3

Recovery of SE from cloacal swabs 1 and 2 weeks post-challenge.

| | 1 wk (% + (# +)) | 2 wk (% + (# +)) |
|---|---|---|
| Control | 70 (14/20) | 25 (5/20) |
| Yeast-PAL-HMGB1 | 40 (4/10) | 0 (0/10)* |

*Different from Control $p < 0.1$

Evaluation of Coccidia Infection after Vaccination with a Yeast Vectored Vaccine Candidate.

We next tested the efficacy of Yeast (*Pichia pastoris*) vectored MPP-TRAP-HMGB1 (SEQ ID NO: 61 linked to SEQ ID NO: 65 linked to SEQ ID NO: 2) to reduce morbidity and mortality after infection with *Eimeria maxima*, M6 strain, after challenge. The expression of MPP-TRAP-HMGB1 was confirmed to be surface expressed by immunofluorescence. Eighty chicks were obtained on the day of hatch from a commercial hatchery. On the day of hatch, chicks were randomly divided into four groups, negative control, positive control, vaccinated with the *Pichia*-MPP-TRAP-HMGB-1 in MCA vaccine by oral gavage at day of hatch and day 14 or vaccinated with the *Pichia*-MPP-TRAP-HMGB-1 in MCA vaccine in the drinking water at day 4 and day 14. Vaccinated chicks were vaccinated with $5\times10^7$ cfu/bird Yeast-MPP-TRAP-HMGB1 by oral gavage or in the drinking water. The mannosylated chitosan adjuvant (MCA) stock solution (1.5% chitosan w:v) was diluted 1:2 with the suspension of *Pichia* (0.5% final concentration). For oral gavage, the MCA (0.5%) plus *Pichia* construct ($1\times10^7$ cells) was delivered in 0.25 mL for both the prime and the boost by oral gavage. For administration in the drinking water, the final concentration of MCA in the drinking water was 0.004% and the final concentration of the *Pichia* was $2.3\times10^6$ cells/mL of drinking water and this was used for both prime and boost administration. All chicks were individually tagged and all chicks (N=20 per group) were commingled except during drinking water vaccination and feed and water were provided ad libitum.

All groups were challenged on day 20 and lesion scores were determined on day 6 post-inoculation. Some oocysts escape from the initial challenge (they pass unchanged) so a very modest challenge is expected in the unchallenged controls in these commingled chicks. On day 20 the positive control birds and both sets of vaccinated birds were challenged with 100,000 *Eimeria maxima* (strain M6) oocytes. At day 26 each bird was scored for lesions using the Johnson and Reid Lesion Score Index. Johnson, J. and W. M. Reid 1970. Experimental Parasitology 28: 30-36. In this lesion score method the numerical scores indicate the following: 0: No gross lesions; 1: Small red petechiae may appear on the serosal side of the mid-intestine, there is no ballooning or thickening of the intestine, though small amounts of orange mucus may be present; 2: Serosal surface may be speckled with numerous red petechiae; intestine may be filled with orange mucus; little or no ballooning of the intestine; thickening of the wall; 3: Intestinal wall is ballooned and thickened, the mucosal surface is roughened; intestinal contents filled with pinpoint blood clots and mucus; 4: the intestinal wall may be ballooned for most of its length; contains numerous blood clots and digested red blood cells giving a characteristic color and putrid odor; the wall is greatly thickened; dead birds are recorded with this score.

Figure 6:
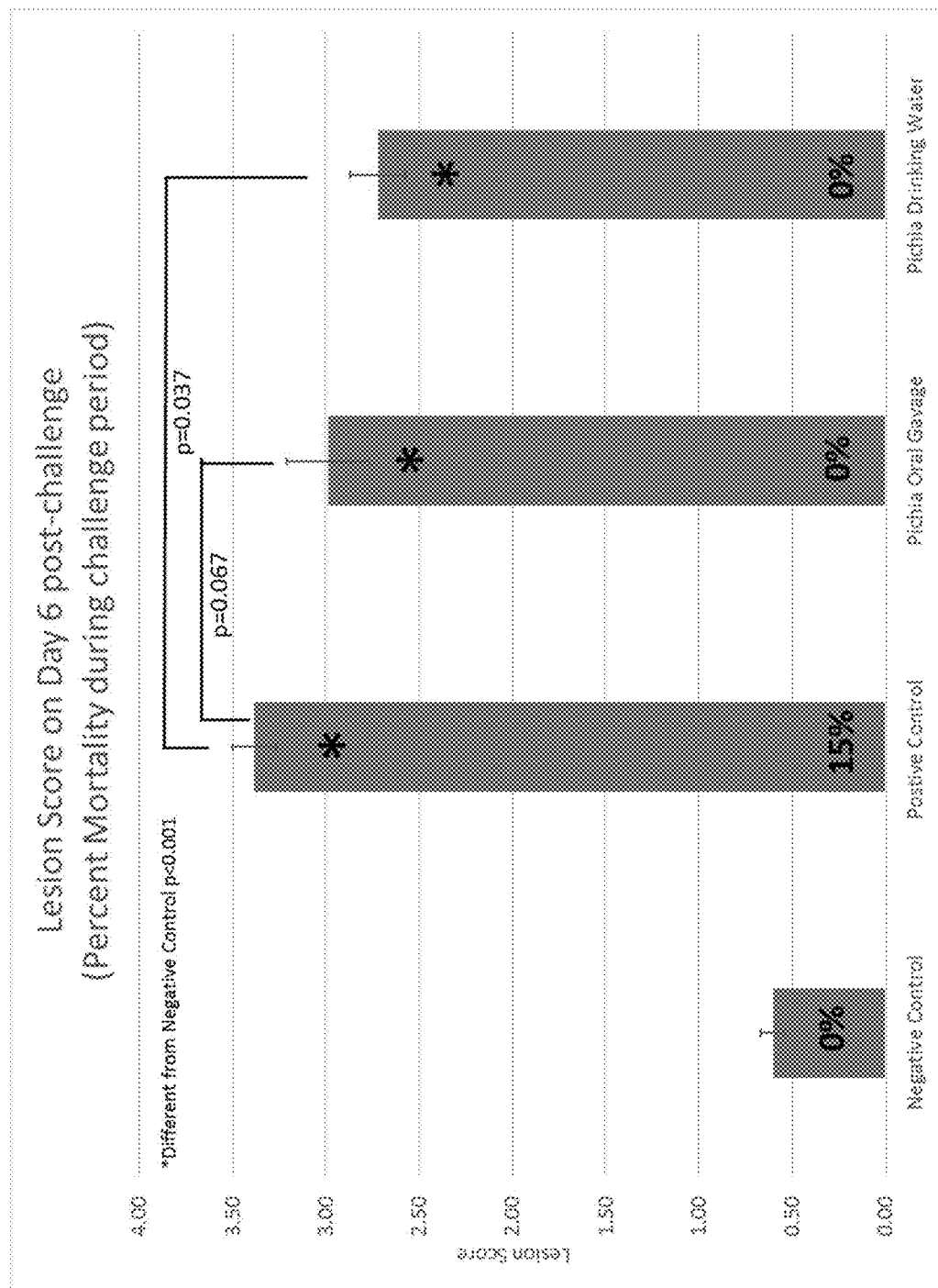
FIG. 6 is a graph showing the percentage of animals having a lesion score of 4 on day 6 post-challenge and the percentage indicated within each bar shows the percent mortality at day 6 post-challenge.

FIG. 6 shows the percent of animals having a lesion score of 4 on day 6 post-challenge and the percentage indicated in each bar shows the percent mortality at day 6 post-challenge. Notably, none of the vaccinated birds died by day 6 as opposed to 15% of the positive control animals. The lesion score was also reduced as shown by the calculated p value shown in FIG. 6 (p=0.037 for drinking water vaccination, p=0.067 for oral gavage). When *Pichia* expressing both MPP and TRAP antigens along with HMGB1 as the immunostimulatory polypeptide was included in drinking water, the lesion scores were significantly reduced. The statistical analyses were carried out as follows. The lesion data were analyzed using a PROC MIXED ANOVA model in SAS, the assumption was made that the difference in severity between a score of 0 and 1 was similar to the difference in severity between a score of 1 and 2, and so on. Under this assumption, score means may be analyzed for the PROC MIXED ANOVA analysis. Lesion scores range from 0 to 4 as described by Johnson and Reid (1970). Tests of random and fixed effects were performed. The differences of means were calculated to determine any significant differences between lesion scores among treatment groups. The data was determined to have a Poisson distribution and a Tukey Kramer test was used to determine whether there were any statistically significant differences between treatment groups.

As shown in FIG. 7, the distribution of all lesion scores was also decreased in the vaccinated animals. The vaccinated animals demonstrated lower lesion scores. Thus vaccination in either the drinking water or via oral gavage resulted in less mortality and less morbidity after challenge with *Eimeria*.

We claim:

1. A genetically engineered yeast comprising a polynucleotide encoding an immunostimulatory, full-length high mobility group box (HMGB1) polypeptide and a GP1-anchored alpha-agglutinin polypeptide from *Saccharomyces cerevisiae*, wherein the HMGB1 polypeptide is connected to the C-terminus of the alpha-agglutinin polypeptide, and wherein the genetically engineered yeast displays the HMGB1 polypeptide on the surface of the yeast.

2. The genetically engineered yeast of claim 1, further comprising a polynucleotide encoding an antigenic polypeptide, wherein the antigenic polypeptide is displayed on the surface of the yeast.

3. The genetically engineered yeast of claim 2, wherein the antigenic polypeptide and the HMGB1 polypeptide are a part of a fusion protein.

4. The genetically engineered yeast of claim 2, wherein the antigenic polypeptide is selected from the group consisting of an Influenza polypeptide, a *Campylobacter* polypeptide, a *Clostridium* polypeptide, a *Salmonella* polypeptide, an *Eimeria* polypeptide, and a tumor associated polypeptide.

5. The genetically engineered yeast of claim 2, wherein the antigenic polypeptide comprises an amino acid sequence selected from the group consisting of SEQ ID NOs: 39 to 56 and SEQ ID NOs: 58 to 93.

6. The genetically engineered yeast of claim 1, wherein the yeast is *Pichia*.

7. The genetically engineered yeast of claim 1, wherein the HMGB1 polypeptide comprises an amino acid sequence with at least 98% identity to a sequence selected from the group consisting of SEQ ID NOs: 2-30 and SEQ ID NOs: 94-105.

8. A pharmaceutical composition comprising the genetically engineered yeast of claim 2 and a pharmaceutically acceptable carrier.

9. The pharmaceutical composition of claim 8, wherein the pharmaceutically acceptable carrier is acceptable for oral or nasal administration.

10. The pharmaceutical composition of claim 8, wherein the yeast is not capable of replication or is inactivated or killed.

11. A method of enhancing an immune response in a vertebrate or mammalian subject by administering the pharmaceutical composition of claim 8 to the subject in an amount effective to enhance the immune response to the antigenic polypeptide in the subject.

12. The method of claim 11, wherein the yeast is not capable of replication or is inactivated or killed.

13. The method of claim 11, wherein the subject is a human, cow, cat, dog, pig, fish, bird or poultry.

* * * * *